US007868008B2

(12) United States Patent
Van Wagenen et al.

(10) Patent No.: US 7,868,008 B2
(45) Date of Patent: *Jan. 11, 2011

(54) SUBSTITUTED ISOINDOLONES AND THEIR USE AS METABOTROPIC GLUTAMATE RECEPTOR POTENTIATORS

(75) Inventors: Bradford Van Wagenen, Salt Lake City, UT (US); Radhakrishnan Ukkiramapandian, Salt Lake City, UT (US); Joshua Clayton, Oakville (CA); Ian Egle, North York (CA); James Empfield, Wilmington, DE (US); Methvin Isaac, Brampton (CA); Fupeng Ma, Melrose, MA (US); Abdelmalik Slassi, Mississauga (CA); Gary Steelman, Wilmington, DE (US); Rebecca Urbanek, Wilmington, DE (US); Sally Walsh, Wilmington, DE (US)

(73) Assignee: AstraZeneca AB, Sodertalje (SE)

(*) Notice: Subject to any disclaimer, the term of this patent is extended or adjusted under 35 U.S.C. 154(b) by 0 days.

This patent is subject to a terminal disclaimer.

(21) Appl. No.: 12/063,018

(22) PCT Filed: Feb. 15, 2006

(86) PCT No.: PCT/US2006/005247
§ 371 (c)(1),
(2), (4) Date: Jul. 23, 2008

(87) PCT Pub. No.: WO2007/021309
PCT Pub. Date: Feb. 22, 2007

(65) Prior Publication Data
US 2009/0111830 A1 Apr. 30, 2009

Related U.S. Application Data

(63) Continuation-in-part of application No. PCT/US2005/028760, filed on Aug. 12, 2005.

(51) Int. Cl.
C07D 209/46 (2006.01)
C07D 401/06 (2006.01)
C07D 401/14 (2006.01)
A61K 31/4035 (2006.01)
A61K 31/454 (2006.01)

(52) U.S. Cl. .......... 514/254.09; 514/323; 514/339; 514/414; 514/421; 544/373; 546/201; 546/277.7; 548/467; 548/472

(58) Field of Classification Search .......... None
See application file for complete search history.

(56) References Cited

U.S. PATENT DOCUMENTS 5,175,157 A 12/1992 Psiorz et al.
5,681,954 A 10/1997 Yamamoto et al.
6,017,919 A * 1/2000 Inaba et al. .......... 514/251
2003/0212094 A1 11/2003 Yamabe
2005/0026976 A1 2/2005 Curtin et al.

FOREIGN PATENT DOCUMENTS

| WO | WO-99/26927 A | 6/1999 |
| WO | WO-2004/031178 A | 4/2004 |
| WO | WO-2005/074643 A | 8/2005 |
| WO | WO-2005/085214 A | 9/2005 |
| WO | WO-2005/085216 A | 9/2005 |
| WO | WO-2006/020879 A | 2/2006 |
| WO | WO-2006/047237 A2 | 5/2006 |
| WO | WO-2006/091496 | 8/2006 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta, S.R. et. al., "Crystalline Solids", Advanced Drug Delivery Reviews, vol. 48, pp. 3-26, 2001.*
Lee et al., "The role of metabotropic glutamate receptors in Alzheimer's disease", Acta Neurobiologiae Experimentalis, 64(1), 89-98, 2004.*
Barr et al.; Journal of Organometallic Chemistry, vol. 302, No. 1, Mar. 11, 1986, pp. 117-126, XP002383544.
Hoarau C et al: Synthesis, No. 5, 2000, pp. 655-660, XP002383545.
Rys V et al: European Journal of Organic Chemistry, No. 7, Apr. 2003, pp. 1231-1237, XP002383546.
Clayden J et al: Organic Letters, vol. 2, No. 26, 2000, pp. 4229-4232 XP002345295.

(Continued)

Primary Examiner—Fiona T Powers
(74) Attorney, Agent, or Firm—Kenneth F. Mitchell

(57) ABSTRACT

The present invention is directed to compounds of formula I:

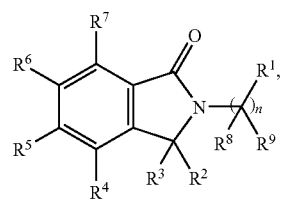

(I)

wherein $R^1, R^2, R^3, R^4, R^5, R^6, R^7, R^8, R^9$ and n are as defined for formula I in the description. The invention also relates to processes for the preparation of the compounds and to new intermediates employed in the preparation, pharmaceutical compositions containing the compounds, and to the use of the compounds in therapy.

4 Claims, No Drawings

OTHER PUBLICATIONS

Couture A et al: Tetrahedron Letters, vol. 43, No. 12, Mar. 18, 2002, pp. 2207-2210 XP004344002.

Casagrande C et al: IL Farmaco, Edizione Scientifica, vol. 27, No. 6, Jun. 1972, pp. 445-470, XP000 571647.

Bonnefous et al., Bioorganic & Medicinal Chemistry Letters, vol. 15, p. 4354-4358 (2005).

Bonnefous et al. (Merck), poster presented at the 229th National Meeting of the American Chemical Society, San Diego, CA, Mar. 2005; poster, MEDI-37.

Eric Mertz, et al, "Synthetic Receptors for CG Base Pairs", Organic Letters, 2000, vol. 2, No. 19, pp. 2931-2934.

Sudha R. Vippagunta, et al, "Crystalline Solids", Advanced Drug Delivery Reviews, 48 (2001), pp. 3-26.

Pierre Souillac, et al., "Characterization of Delivery Systems, Differential Scanning Calorimetry in Encyclopedia of Controlled Drug Delivery", 1999, John Wiley & Sons, pp. 212-227.

Hyoung-Gon Lee, et al, "The Role of Metabotropic Glutamate Receptors in Alzheimer's Disease", Acta Neurobiol Exp 2004, 64: pp. 89-98.

* cited by examiner

SUBSTITUTED ISOINDOLONES AND THEIR USE AS METABOTROPIC GLUTAMATE RECEPTOR POTENTIATORS

CROSS REFERENCE TO RELATED APPLICATIONS

This application is a Continuation-In-Part of PCT Application PCT/US05/28760, filed Aug. 12, 2005, which is incorporated herein by reference in its entirety.

BACKGROUND OF THE INVENTION

The present invention relates to novel compounds that function as potentiators of glutamate receptors, methods for their preparation, pharmaceutical compositions containing them and their use in therapy.

The metabotropic glutamate receptors (mGluR) constitute a family of GTP-binding-protein (G-protein) coupled receptors that are activated by glutamate, and have important roles in synaptic activity in the central nervous system, including neural plasticity, neural development and neurodegeneration.

Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels (Schoepp et al., 1993, Trends Pharmacol. Sci., 14:13; Schoepp, 1994, Neurochem. Int., 24:439; Pin et al., 1995, Neuropharmacology 34:1; Bordi & Ugolini, 1999, Prog. Neurobiol. 59:55).

Eight mGluR subtypes have been identified, which are divided into three groups based upon primary sequence similarity, signal transduction linkages, and pharmacological profile. Group-I includes mGluR1 and mGluR5, which activate phospholipase C and the generation of an intracellular calcium signal. The Group-II (mGluR2 and mGluR3) and Group-III (mGluR4, mGluR6, mGluR7, and mGluR8) mGluRs mediate an inhibition of adenylyl cyclase activity and cyclic AMP levels. For a review, see Pin et al., 1999, Eur. J. Pharmacol., 375:277-294.

Activity of mGluR family receptors are implicated in a number of normal processes in the mammalian CNS, and are important targets for compounds for the treatment of a variety of neurological and psychiatric disorders. Activation of mGluRs is required for induction of hippocampal long-term potentiation and cerebellar long-term depression (Bashir et al., 1993, Nature, 363:347; Bortolotto et al., 1994, Nature, 368:740; Aiba et al., 1994, Cell, 79:365 Aiba et al., 1994, Cell, 79:377). A role for mGluR activation in nociception and analgesia also has been demonstrated (Meller et al., 1993, Neuroreport, 4: 879; Bordi & Ugolini, 1999, Brain Res., 871:223). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex (Nakanishi, 1994, Neuron, 13:1031; Pin et al., 1995, Neuropharmacology, supra; Knopfel et al., 1995, J. Med. Chem., 38:1417).

Recent advances in the elucidation of the neurophysiological roles of mGluRs have established these receptors as promising drug targets in the therapy of acute and chronic neurological and psychiatric disorders and chronic and acute pain disorders. Because of the physiological and pathophysiological significance of the mGluRs, there is a need for new drugs and compounds that can modulate mGluR function.

SUMMARY OF THE INVENTION

We have identified a class of compounds that modulate mGluR function. In one aspect the invention provides compounds of formula I,

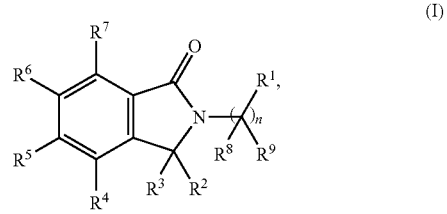

(I)

wherein:
$R^1$ is a 3- to 7-membered ring that may contain one or more heteroatoms independently selected from the group consisting of N, O and S, wherein said ring may be substituted by one or more A;

$R^2$ and $R^3$ are independently selected from the group consisting of H, $C_{1-6}$-alkyl, $C_{2-6}$-alkenyl, $C_{2-6}$-alkynyl, aryl, heteroaryl, heterocycloalkyl, $C_{3-8}$-cycloalkyl, $C_{1-6}$-alkyl-aryl, $C_{1-6}$-alkylheteroaryl, $C_{1-6}$-alkyl-heterocycloalkyl, and $C_{1-6}$-alkyl-$C_{3-8}$-cycloalkyl, wherein $R^2$ and $R^3$ may be substituted by one or more A;

$R^4$ and $R^6$ are independently selected from the group consisting of H, hydroxy, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $(CO)R^{10}$, $O(CO)R^{10}$, $O(CO)OR^{10}$, $C(O)OR^{10}$, $O(CNR^{10})OR^{11}$, $C_{1-6}$-alkylOR$^{10}$, $OC_{2-6}$-alkylOR$^{10}$, $C_{1-6}$-alkyl(CO)R$^{10}$, $OC_{1-6}$-alkyl(CO)R$^{10}$, $C_{0-6}$-alkylCO$_2$R$^{10}$, $OC_{1-6}$-alkylCO$_2$R$^{10}$, $C_{1-6}$-alkylcyano, $OC_{2-6}$-alkylcyano, $C_{0-6}$-alkylNR$^{10}$R$^{11}$, $OC_{2-6}$-alkylNR$^{10}$R$^{11}$, $C_{1-6}$-alkyl(CO)NR$^{10}$R$^{11}$, $OC_{0-6}$-alkyl(CO)NR$^{10}$R$^{11}$, $C_{0-6}$-alkylNR$^{10}$(CO)R$^{11}$, $OC_{2-6}$-alkylNR$^{10}$(CO)R$^{11}$, $C_{0-6}$-alkylNR$^{10}$(CO) NR$^{10}$R$^{11}$, $C_{0-6}$-alkylSR$^{10}$, $OC_{2-6}$-alkylSR$^{10}$, $C_{0-6}$-alkyl (SO)R$^{10}$, $OC_{2-6}$-alkyl(SO)R$^{10}$, $C_{1-6}$-alkylSO$_2$R$^{10}$, $OC_{2-6}$-alkylSO$_2$R$^{10}$, $C_{0-6}$-alkyl(SO$_2$)NR$^{10}$R$^{11}$, $OC_{2-6}$-alkyl(SO$_2$)NR$^{10}$R$^{11}$, $C_{0-6}$-alkylNR$^{10}$(SO$_2$)R$^{11}$, $OC_{2-6}$-alkylNR$^{10}$(SO$_2$)R$^{11}$, $C_{0-6}$-alkylNR$^{10}$(SO$_2$)NR$^{10}$R$^{11}$, $OC_{2-6}$-alkylNR$^{10}$(SO$_2$)NR$^{10}$R$^{11}$, $(CO)NR$^{10}$R$^{11}$, $O(CO)$ NR$^{10}$R$^{11}$, NR$^{10}$OR$^{11}$, $C_{0-6}$-alkylNR$^{10}$(CO)OR$^{11}$, $OC_{2-6}$-alkylNR$^{10}$(CO)OR$^{11}$, SO$_3$R$^{10}$ and a 5- to 7-membered ring that may contain one or more heteroatoms independently selected from the group consisting of N, O and S, wherein $R^4$ and $R^6$ may be substituted by one or more A, and wherein any cycloalkyl or aryl is optionally fused to a 5- to 7-membered ring that may contain one or more heteroatoms independently selected from the group consisting of C, N, O and S;

$R^5$ is selected from the group consisting of CN, $OC_{0-6}$-alkyl, $C_{3-8}$-cycloalkyl, $C_{1-6}$-alkyl-$C_{3-8}$-cycloalkyl, $OC_{0-6}$-alkyl-$C_{3-8}$-cycloalkyl, $C_{0-6}$-alkylaryl, $OC_{0-6}$-alkylaryl, $C_{0-6}$- alkylheteroaryl, $OC_{0-6}$-alkylheteroaryl, heterocycloalkyl, $C_{1-6}$-alkylheterocycloalkyl, $OC_{0-6}$-alkylheterocycloalkyl and $C(O)R_{10}$, wherein any cyclic moiety is substituted by one or more B;

$R^7$ is selected from the group consisting of H, F, Cl, Br, I, nitro, cyano, $OC_{1-4}$-alkyl, $C_{1-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, and $C_{3-8}$-cycloalkyl;

$R^8$ and $R^9$ are independently selected from the group consisting of H, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, and $OC_{2-6}$-alkynyl, or, where n is greater than 1, two or more $R^8$ and/or $R^9$ on adjacent carbon atoms may be absent to form an alkenyl or alkynyl moiety;

$R^{10}$ and $R^{11}$ are independently selected from the group consisting of H, hydroxy, oxo, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{0-6}$-alkyl-heterocycloalkyl, $OC_{1-6}$-alkyl-heterocycloalkyl, heteroaryl, $C_{1-6}$alkylheteroaryl, heterocycloalkyl-$C_{1-6}$-alkylaryl and heterocycloalkyl-$C_{1-6}$-alkylheteroaryl, wherein any cyclic moiety is optionally fused to a 5- to 7-membered ring that may contain one or more heteroatoms independently selected from the group consisting of C, N, O and S and any cyclic moiety is optionally substituted with a substituent selected from alkyl, halo, hydroxyl, Oalkyl, haloalkyl and Ohaloalkyl;

A is selected from the group consisting of H, hydroxy, F, Cl, Br, I, nitro, cyano, oxo, $C_{1-6}$-alkyl, $C_{1-6}$-alkylhalo, $OC_{1-6}$ alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{1-6}$-alkyl-heterocyclyl, $C_{1-6}$-alkyl-heterocycloalkyl, $OC_{0-6}$-alkyl-heterocycloalkyl, $(CO)R^{10}$, $O(CO)R^{10}$, $O(CO)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{0-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{1-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}OR^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein said 5- to 7-membered ring is optionally substituted by one or more of $R^{10}$ and $R^{11}$;

B is selected from the group consisting of $C_{0-6}$-alkyl-$C_{3-8}$-cycloalkyl, $OC_{0-6}$-alkyl-$C_{3-8}$-cycloalkyl, $C_{0-6}$-alkylaryl, $OC_{0-6}$-alkylaryl, $C_{1-6}$-alkylheterocycloalkyl, $OC_{0-6}$ alkyl-heterocycloalkyl, $C_{1-6}$-alkylheteroaryl and $OC_{1-6}$-alkyl-heteroaryl, wherein any cyclic moiety is substituted with at least one substituent selected from the group consisting of halo, alkyl alkylhalo, alkoxy, oxo, COR, $CO_2R$, $SO_2R$ and CN;

R is selected from the group consisting of H and alkyl;

and n is selected from the group consisting of 1, 2, 3, 4, 5, 6, 7, and 8;

or a pharmaceutically acceptable salt, hydrate, solvate, optical isomer, or combination thereof.

The invention also provides processes for the preparation of compounds of formula I.

The invention further provides a pharmaceutical composition comprising a compound according to formula I together with a pharmaceutically acceptable carrier or excipient; in another aspect the invention provides a method for the treatment or prevention of neurological and psychiatric disorders associated with glutamate dysfunction in an animal in need of such treatment. The method comprises the step of administering to the animal a therapeutically effective amount of a compound of formula I or a pharmaceutical composition thereof.

The invention also provides for the use of a compound according to formula I, or a pharmaceutically acceptable salt or solvate thereof in the manufacture of a medicament for the treatment of any of the conditions discussed herein. Further, the invention provides a compound of formula I, or a pharmaceutically acceptable salt or solvate thereof, for use in therapy.

DETAILED DESCRIPTION OF THE PREFERRED EMBODIMENTS

The present invention is based upon the discovery of compounds that exhibit activity as pharmaceuticals, in particular as modulators of metabotropic glutamate receptors. More particularly, the compounds of the present invention exhibit activity as potentiators of the mGluR2 receptor, and are useful in therapy, in particular for the treatment of neurological and psychiatric disorders associated with glutamate dysfunction.

Definitions

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "alkyl" as used herein means a straight- or branched-chain hydrocarbon radical having, for example, from one to six carbon atoms, and includes methyl)ethyl, propyl, isopropyl, t-butyl and the like.

The term "alkenyl" as used herein means a straight- or branched-chain alkenyl radical having, for example, from two to six carbon atoms, and includes ethenyl, 1-propenyl, 1-butenyl and the like.

The term "alkynyl" as used herein means a straight- or branched-chain alkynyl radical having, for example, from two to six carbon atoms, and includes 1-propynyl (propargyl), 1-butynyl and the like.

The term "cycloalkyl" as used herein means a cyclic group (which may be unsaturated) having, for example, from three to seven carbon atoms, and includes cyclopropyl, cyclohexyl, cyclohexenyl and the like.

The term "heterocycloalkyl" as used herein means, for example, a three- to seven-membered cyclic group (which may be unsaturated) having at least one heteroatom selected from the group consisting of N, S and O, and includes piperidinyl, piperazinyl, pyrrolidinyl, tetrahydrofuranyl and the like.

The term "alkoxy" as used herein means a straight- or branched-chain alkoxy radical having, for example, from one to six carbon atoms and includes methoxy, ethoxy, propyloxy, isopropyloxy, t-butoxy and the like.

The term "halo" as used herein means halogen and includes fluoro, chloro, bromo, iodo and the like, in both radioactive and non-radioactive forms.

The term "aryl" as used herein means an aromatic group having, for example, five to twelve atoms, and includes phenyl, naphthyl and the like.

The term "heteroaryl" means an aromatic group which includes at least one heteroatom selected from the group consisting of N, S and O, and includes groups and includes pyridyl, indolyl, furyl, benzofuryl, thienyl, benzothienyl, quinolyl, oxazolyl and the like.

The term "alkanoyl" as used herein means a straight- or branched-chain alkanoyl radical having, for example, from two to seven atoms, and includes acetyl, propionyl, butyryl and the like.

The term "cycloalkenyl" as used herein means an unsaturated cycloalkyl group having, for example, from four to seven carbon atoms, and includes cyclopent-1-enyl, cyclohex-1-enyl and the like.

The terms "alkylaryl", "alkylheteroaryl" and "alkylcycloalkyl" refer to an alkyl radical substituted with an aryl, heteroaryl or cycloalkyl group, and includes 2-phenethyl, 3-cyclohexyl propyl and the like.

The term "5- to 7-membered ring that may contain one or more heteroatoms independently selected from N, O and S" includes aromatic and heteroaromatic rings, as well as carbocyclic and heterocyclic rings which may be saturated or unsaturated, and includes furyl, isoxazolyl, oxazolyl, pyrazolyl, pyridazinyl, pyridyl, pyrimidyl, pyrrolyl, thiazolyl, thienyl, imidazolyl, triazolyl, morpholinyl, piperazinyl, piperidinyl, homopiperidinyl, tetrahydropyranyl, phenyl, cyclohexyl, cycloheptyl, cyclopentyl, cyclohexanyl and the like.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Compounds

Compounds of the invention conform generally to formula I:

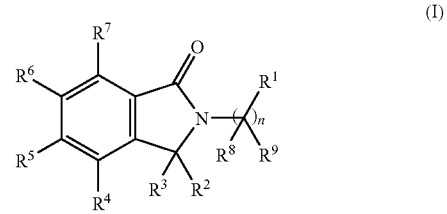

(I)

wherein:

$R^1$ is a 3- to 7-membered ring that may contain one or more heteroatoms independently selected from the group consisting of N, O and S, wherein said ring may be substituted by one or more A;

$R^2$ and $R^3$ are independently selected from the group consisting of H, $C_{1-6}$-alkyl, $C_{2-6}$-alkenyl, $C_{2-6}$-alkynyl, aryl, heteroaryl, heterocycloalkyl, $C_{3-8}$-cycloalkyl, $C_{1-6}$-alkyl-aryl, $C_{1-6}$-alkyl-heteroaryl, $C_{1-6}$-alkyl-heterocycloalkyl, and $C_{1-6}$-alkyl-$C_{3-8}$-cycloalkyl, wherein $R^2$ and $R^3$ may be substituted by one or more A;

$R^4$ and $R^6$ are independently selected from the group consisting of H, hydroxy, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $(CO)R^{10}$, $O(CO)R^{10}$, $O(CO)OR^{10}$, $C(O)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{1-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkylS$R^{10}$, $OC_{2-6}$-alkylS$R^{10}$, $C_{0-6}$-alkyl$(SO)R^{10}$, $OC_{2-6}$-alkyl$(SO)R^{10}$, $C_{0-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}OR^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein $R^4$ and $R^6$ may be substituted by one or more A, and wherein any cycloalkyl or aryl is optionally fused to a 5- to 7-membered ring that may contain one or more heteroatoms independently selected from the group consisting of C, N, O and S;

$R^5$ is selected from the group consisting of CN, $OC_{0-6}$-alkyl, $C_{3-8}$-cycloalkyl, $C_{1-6}$-alkyl-$C_{3-8}$-cycloalkyl, $OC_{0-6}$-alkyl-$C_{3-8}$-cycloalkyl, $C_{0-6}$-alkylaryl, $OC_{0-6}$-alkylaryl, $C_{0-6}$-alkylheteroaryl, $OC_{0-6}$-alkylheteroaryl, heterocycloalkyl, $C_{1-6}$-alkylheterocycloalkyl, $OC_{0-6}$-alkylheterocycloalkyl and $C(O)R^{10}$, wherein any cyclic moiety is substituted by one or more B;

$R^7$ is selected from the group consisting of H, F, Cl, Br, I, nitro, cyano, $OC_{1-4}$-alkyl, $C_{1-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, and $C_{3-8}$-cycloalkyl;

$R^8$ and $R^9$ are independently selected from the group consisting of H, F, Cl, Br, I, nitro, cyano, $C_{1-6}$-alkyl, $C_{1-6}$-alkylhalo, $OC_{1-6}$-alkyl, $OC_{1-6}$-alkylhalo, $C_{2-6}$-alkenyl, $OC_{2-6}$-alkenyl, $C_{2-6}$-alkynyl, and $OC_{2-6}$-alkynyl,
or, where n is greater than 1,
two or more $R^8$ and/or $R^9$ on adjacent carbon atoms may be absent to form an alkenyl or alkynyl moiety;

$R^{10}$ and $R^{11}$ are independently selected from the group consisting of H, hydroxy, oxo, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{0-6}$-alkyl-heterocycloalkyl, $OC_{1-6}$-alkyl-heterocycloalkyl, heteroaryl, $C_{1-6}$alkylheteroaryl, heterocycloalkyl-$C_{1-6}$-alkylaryl and heterocycloalkyl-$C_{1-6}$-alkylheteroaryl, wherein any cyclic moiety is optionally fused to a 5- to 7-membered ring that may contain one or more heteroatoms independently selected from the group consisting of C, N, O and S and any cyclic moiety is optionally substituted with a substituent selected from alkyl, halo, hydroxyl, Oalkyl, haloalkyl and Ohaloalkyl;

A is selected from the group consisting of H, hydroxy, F, Cl, Br, I, nitro, cyano, oxo, $C_{1-6}$-alkyl, $C_{1-6}$-alkylhalo, $OC_{1-6}$ alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{1-6}$-alkyl-heterocyclyl, $C_{1-6}$-alkyl-heterocycloalkyl, $OC_{0-6}$-alkyl-heterocycloalkyl, $(CO)R^{10}$, $O(CO)R^{10}$, $O(CO)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{0-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkylS$R^{10}$, $OC_{2-6}$-alkylS$R^{10}$, $C_{0-6}$-alkyl$(SO)R^{10}$), $OC_{2-6}$-alkyl$(SO)R^{10}$, $C_{1-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}OR^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein said 5- to 7-membered ring is optionally substituted by one or more of $R^{10}$ and $R^{11}$;

B is selected from the group consisting of $C_{0-6}$-alkyl-$C_{3-8}$-cycloalkyl, $OC_{0-6}$-alkyl-$C_{3-8}$-cycloalkyl, $C_{0-6}$-alkylaryl, $OC_{0-6}$-alkylaryl, $C_{1-6}$-alkylheterocycloalkyl, $OC_{0-6}$-alkyl-heterocycloalkyl, $C_{1-6}$-alkylheteroaryl and $C_{1-6}$-alkylheteroaryl, wherein any cyclic moiety is substituted with at least one substituent selected from the group consisting of halo, alkyl, alkylhalo, alkoxy, oxo, COR, $CO_2R$, $SO_2R$ and CN;

R is selected from the group consisting of H and alkyl; and n is selected from the group consisting of 1, 2, 3, 4, 5, 6, 7, and 8;

or a pharmaceutically acceptable salt hydrate, solvate, optical isomer, or combination thereof;

with the proviso that the compound is not selected from the group consisting of:

5-(4-Benzyl-piperazine-1-carbonyl)-7-methyl-2-(4-trifluoromethoxy-benzyl)-2,3-dihydro-isoindol-1-one, 7-Methyl-5-(4-pyridin-4-ylmethyl-piperazine-1-carbonyl)-2-(4-trifluoromethoxy-benzyl)-2,3-dihydro-isoindol-1-one, 7-Methyl-5-[4-(2-pyridin-4-yl-ethyl)piperazine-1-carbonyl]-2-(4-trifluoromethoxy-benzyl)-2,3-dihydro-isoindol-1-one, 4-{4-[7-Methyl-1-oxo-2-(4-trifluoromethoxy-benzyl)-2,3-dihydro-1H-isoindol-5-ylmethyl]-piperidin-1-ylmethyl}-benzonitrile, 2-Benzyl-1-oxo-2,3-dihydro-1H-isoindole-5-carbonitrile, 7-Chloro-1-oxo-2-(4-trifluoromethoxy-benzyl)-2,3-dihydro-1H-isoindole-5-carbonitrile, 7-Methyl-1-oxo-2-(4-trifluoromethoxy-benzyl)-2,3-dihydro-1H-isoindole-5-carbonitrile, 7-Methyl-1-oxo-2-(4-chloro-benzyl)-2,3-dihydro-1H-isoindole-5-carbonitrile, 1-Oxo-2-(4-trifluoromethoxy-benzyl)-7-trifluoromethyl-2,3-dihydro-1H-isoindole-5-carbonitrile, 3-Oxo-2-(4-trifluoromethoxy-benzyl)-2,3-dihydro-1H-isoindole-4,6-dicarbonitrile, 7-Iodo-5-methoxy-2-(4-trifluoromethoxy-benzyl)-2,3-dihydro-isoindol-1-one, 2-Benzyl-5-methoxy-2,3-dihydro-isoindol-1-one, and 7-Chloro-5-methoxy-2-(4-trifluoromethoxy-benzyl)-2,3-dihydro-isoindol-1-one.

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of formula I. The optically active forms of the compound of the invention may be prepared, for example, by chiral chromatographic separation of a racemate, by synthesis from optically active starting materials or by asymmetric synthesis based on the procedures described thereafter.

It will also be appreciated by those of skill in the art that certain compounds of the present invention may exist as geometrical isomers, for example E and Z isomers of alkenes. The present invention includes any geometrical isomer of a compound of formula I. It will further be understood that the present invention encompasses tautomers of the compounds of formula I.

It will also be understood by those of skill in the art that certain compounds of the present invention may exist in solvated, for example hydrated, as well as unsolvated forms. It will further be understood that the present invention encompasses all such solvated forms of the compounds of formula I.

Within the scope of the invention are also salts of the compounds of formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment of the present invention, the compound of formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

In a particular embodiment of the invention, $R^5$ is selected from the group consisting of heterocycloalkyl and $C_{1-6}$alkylheterocycloalkyl.

In a particular embodiment of the invention, B is selected from the group consisting of $C_{0-6}$alkylaryl, $C_{1-6}$alkylheteroaryl and $C_{0-6}$alkylheterocycloalkyl.

Specific examples of the present invention include the compounds shown in the following table, their pharmaceutically acceptable salts, hydrates, solvates, optical isomers, and combinations thereof:

| Example No. | Structure | Name |
|---|---|---|
| 5 | 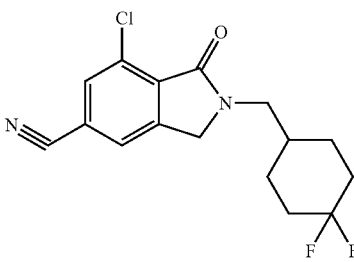 | 7-Chloro-2-[(4,4-difluorocyclohexyl) methyl]-1-oxoisoindoline-5-carbonitrile |
| 8.1 | 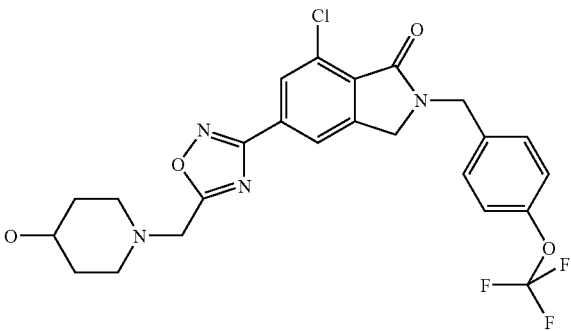 | 7-Chloro-5-[5-(4-hydroxypiperidin-1-yl methyl)-[1,2,4] oxadiazol-3-yl]-2-(4-trifluoromethoxybenzyl)-2,3-dihydro-isoindol-1-one |

-continued

| Example No. | Structure | Name |
|---|---|---|
| 8.2 | 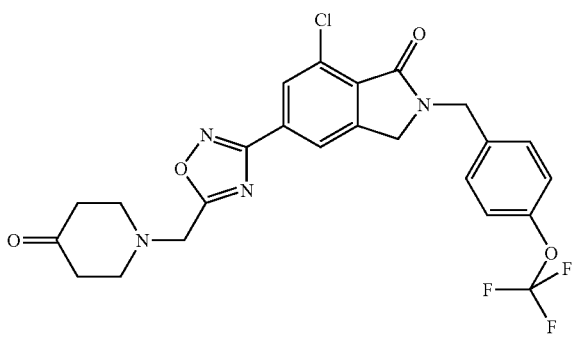 | 7-Chloro-5-[5-(4-oxo-piperidin-1-yl methyl)-[1,2,4]oxadiazol-3-yl]-2-(4-trifluoromethoxy-benzyl)-2,3-dihydro-isoindol-1-one |
| 8.3 | 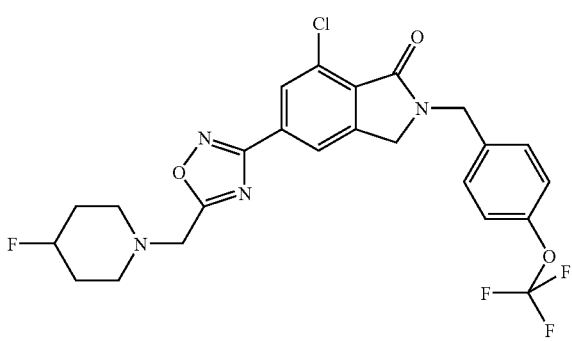 | 7-Chloro-5-[5-(4-fluoro-piperidin-1-yl methyl)-[1,2,4] oxadiazol-3-yl]-2-(4-trifluoromethoxy-benzyl)-2,3-dihydro-isoindol-1-one |
| 8.4 | 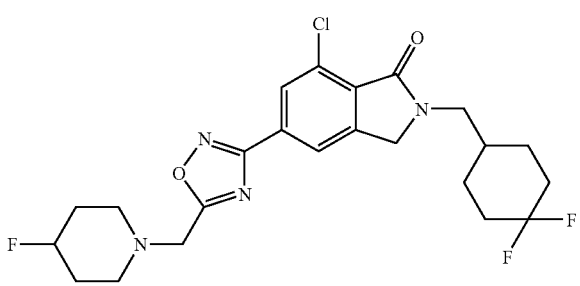 | 7-Chloro-2-(4,4-difluoro-cyclohexyl-methyl)-5-[5-(4-fluoro-piperidin-1-ylmethyl)-[1,2,4]oxadiazol-3-yl]-2,3-dihydro-isoindol-1-one |
| 10.4 | 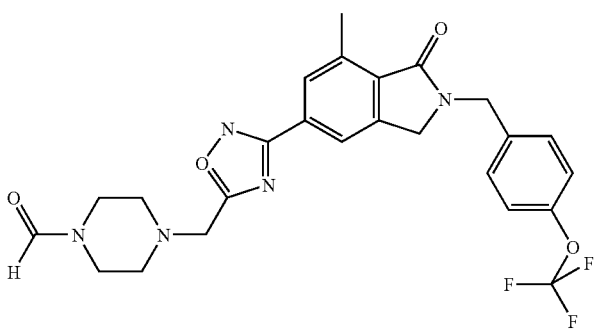 | 4-{5-[7-Methyl-1-oxo-2-(4-trifluoro-methoxy-benzyl)-2,3-dihydro-1H-isoindol-5-yl]-[1,2,4]oxadiazol-3-ylmethyl}-piperazine-1-carbaldehyde |
| 11 | 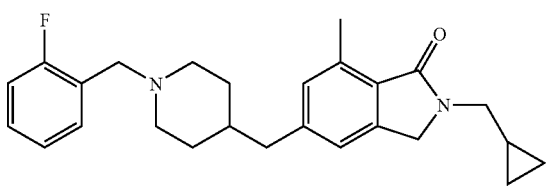 | 2-Cyclopropylmethyl-5-[1-(2-fluoro-benzyl)-piperidin-4-ylmethyl]-7-methyl-2,3-dihydro-isoindol-1-one |

-continued

| Example No. | Structure | Name |
|---|---|---|
| 12.2 | 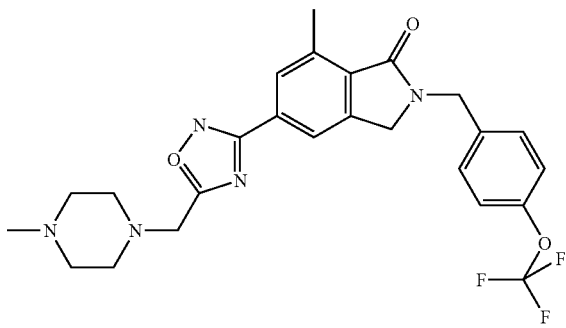 | 7-Methyl-5-[3-(4-methyl-piperazin-1-ylmethyl)-[1,2,4]oxadiazol-5-yl]-2-(4-trifluoromethoxy-benzyl)-2,3-dihydro-isoindol-3-one |
| 12.3 | 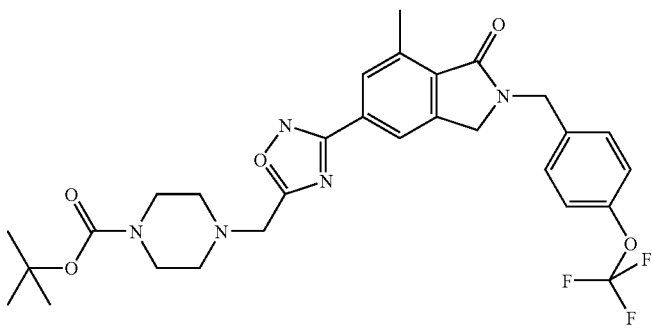 | 4-{5-[7-Methyl-1-oxo-2-(4-trifluoro-methoxy-benzyl)-2,3-dihydro-1H-isoindol-5-yl]-[1,2,4]oxadiazol-3-yl methyl}-piperazine-1-carboxylic acid tert-butyl ester |
| 13.1 | 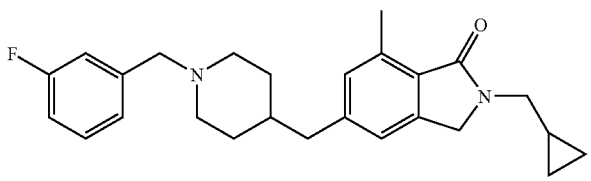 | 2-Cyclopropylmethyl-5-[1-(3-fluoro-benzyl)-piperidin-4-yl methyl]-7-methyl-2,3-dihydro-isoindol-1-one |
| 13.2 | 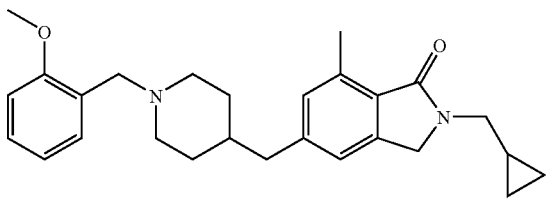 | 2-Cyclopropylmethyl-5-[1-(2-methoxy-benzyl)-piperidin-4-yl methyl]-7-methyl-2,3-dihydro-isoindol-1-one |
| 13.3 | 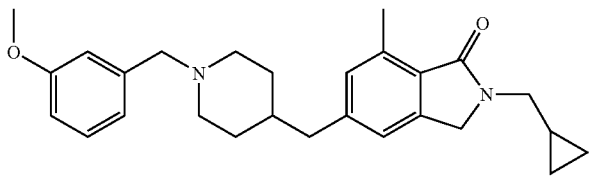 | 2-Cyclopropylmethyl-5-[1-(3-methoxy-benzyl)-piperidin-4-yl methyl]-7-methyl-2,3-dihydro-isoindol-3-one |
| 13.4 | 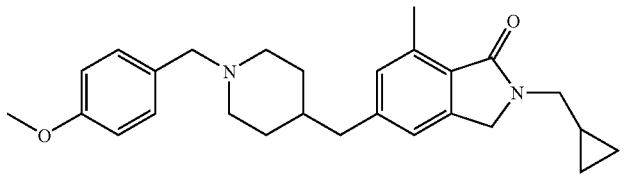 | 2-Cyclopropylmethyl-5-[1-(4-methoxy-benzyl)-piperidin-4-yl methyl]-7-methyl-2,3-dihydro-isoindol-1-one |

-continued

| Example No. | Structure | Name |
|---|---|---|
| 13.5 | 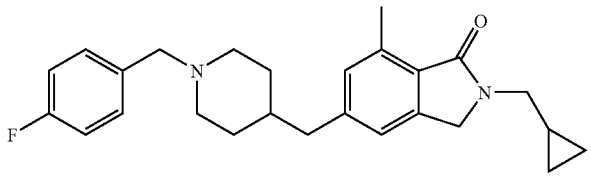 | 2-Cyclopropylmethyl-5-[1-(4-fluoro-benzyl)-piperidin-4-ylmethyl]-7-methyl-2,3-dihydro-isoindol-1-one |
| 13.6 | 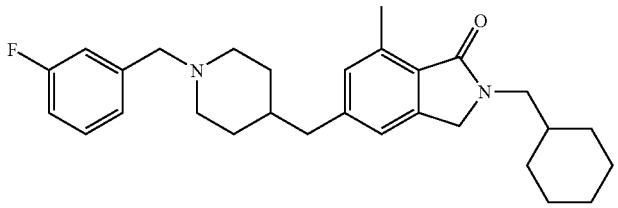 | 2-Cyclohexylmethyl-5-[1-(3-fluoro-benzyl)-piperidin-4-ylmethyl]-7-methyl-2,3-dihydro-isoindol-1-one |
| 13.7 | 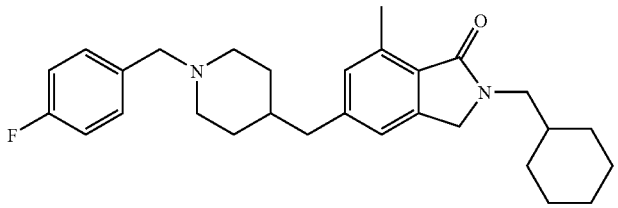 | 2-Cyclohexylmethyl-5-[1-(4-fluoro-benzyl)-piperidin-4-ylmethyl]-7-methyl-2,3-dihydro-isoindol-1-one |
| 13.8 | 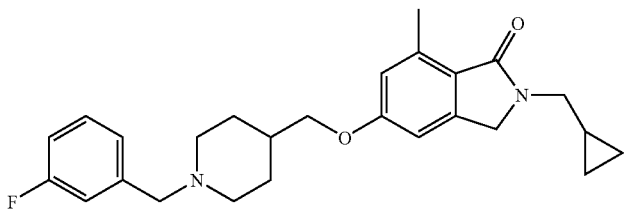 | 2-Cyclopropylmethyl-5-[1-(3-fluoro-benzyl)-piperidin-4-ylmethoxy]-7-methyl-2,3-dihydro-isoindol-1-one |
| 13.9 | 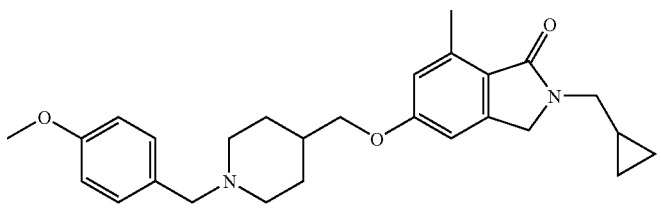 | 2-Cyclopropylmethyl-5-[1-(4-methoxybenzyl)-piperidin-4-ylmethoxy]-7-methyl-2,3-dihydro-isoindol-1-one |
| 15 | 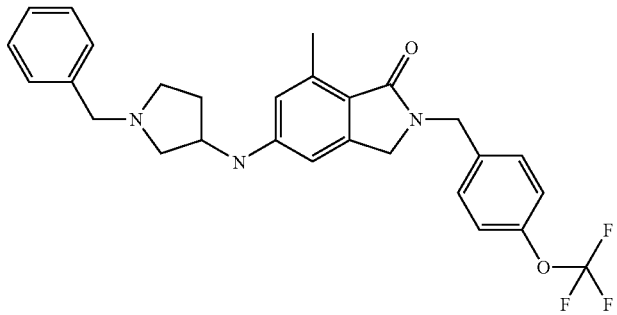 | 5-(1-Benzyl-pyrrolidin-3-ylamino)-7-methyl-2-(4-trifluoromethoxy-benzyl)-2,3-dihydro-isoindol-1-one |

-continued

| Example No. | Structure | Name |
|---|---|---|
| 16.1 | 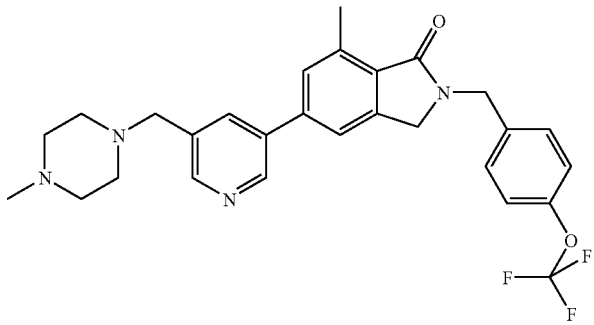 | 7-Methyl-5-[5-(4-methyl-piperazin-1-yl methyl)-pyridin-3-yl] 2-(4-trifluoro methoxy-benzyl)-2,3-dihydro-isoindol-1-one |
| 16.2 | 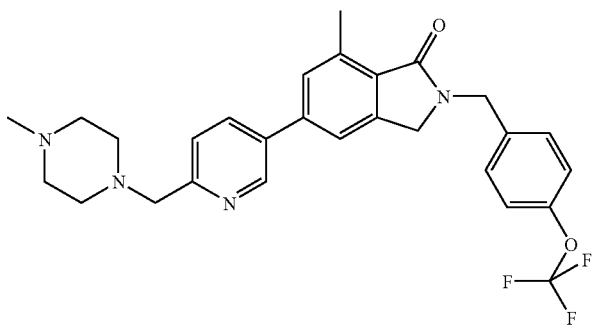 | 7-Methyl-5-[6-(4-methyl-piperazin-1-ylmethyl)-pyridin-3-yl]-2-(4-trifluoro methoxy-benzyl)-2,3-dihydro-isoindol-1-one |
| 17.1 | 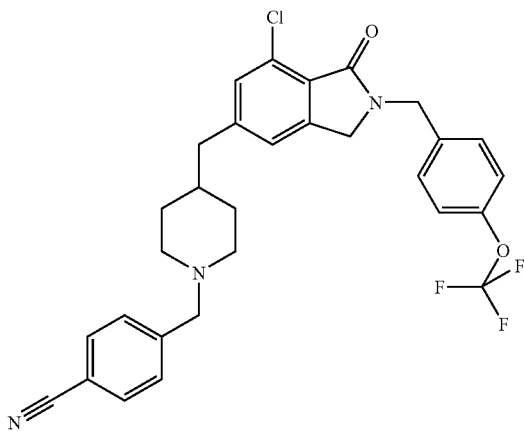 | 4-{4-[7-Chloro-1-oxo-2-(4-trifluoro methoxy-benzyl)-2,3-dihydro-1H-isoindol-5-ylmethyl]-piperidin-1-ylmethyl}-benzonitrile |
| 17.2 | 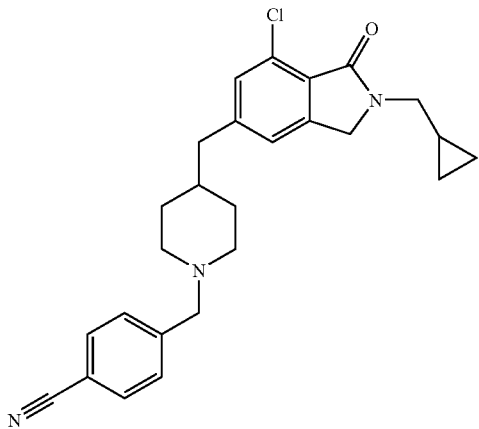 | 4-[4-(7-Chloro-2-cyclopropylmethyl-1-oxo-2,3-dihydro-1H-isoindol-5-yl methyl)-piperidine-1-ylmethyl]-benzonitrile |

| Example No. | Structure | Name |
|---|---|---|
| 17.3 | 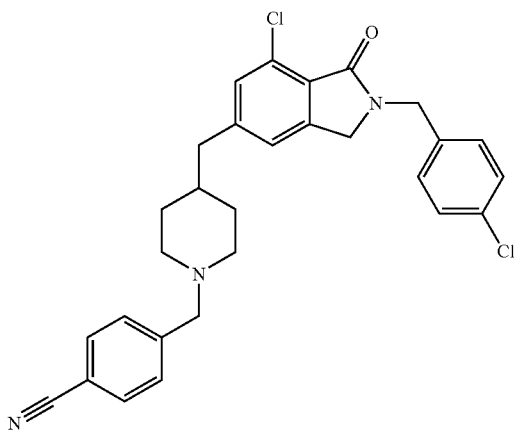 | 4-{4-[7-Chloro-2-(4-chloro-benzyl)-1-oxo-2,3-dihydro-1H-isoindol-5-yl methyl]-piperidin-1-ylmethyl}-benzonitrile |
| 17.4 | 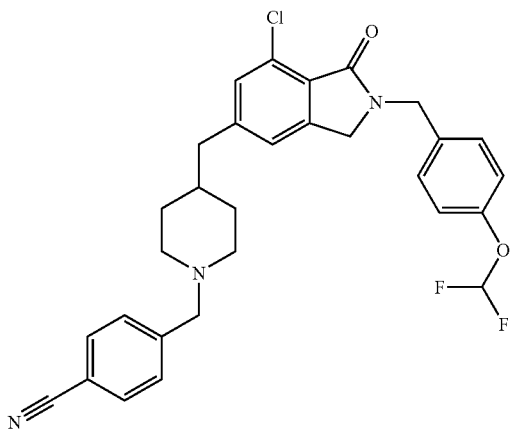 | 4-{4-[7-Chloro-2-(4-difluoromethoxy-benzyl)-1-oxo-2,3-dihydro-1H-isoindol-5-ylmethyl]-piperidin-1-ylmethyl}-benzonitrile |
| 17.5 | 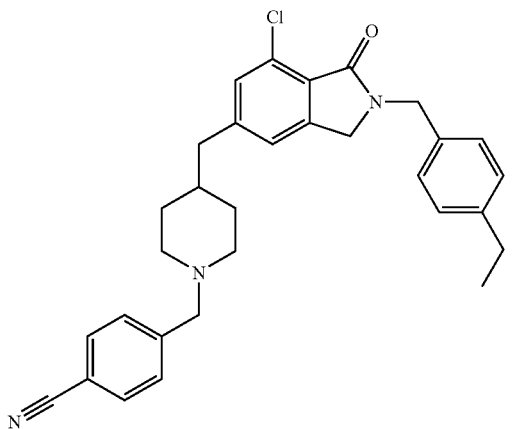 | 4-{4-[7-Chloro-2-(4-ethyl-benzyl)-1-oxo-2,3-dihydro-1H-isoindol-5-yl methyl]-piperidin-1-ylmethyl}-benzonitrile |

-continued

| Example No. | Structure | Name |
|---|---|---|
| 18.1 | 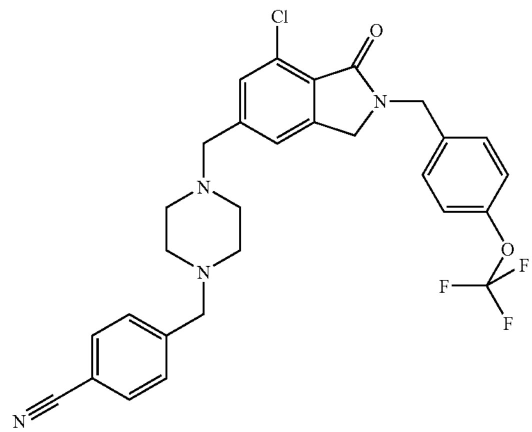 | 4-{4-[7-Chloro-1-oxo-2-(4-trifluoro methoxy-benzyl)-2,3-dihydro-1H-isoindol-5-ylmethyl]-piperazin-1-methyl}-nicotinonitrile |
| 18.2 | 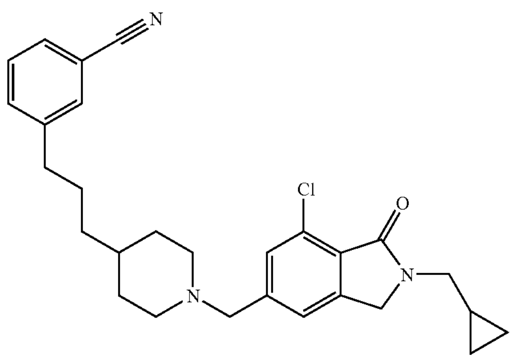 | 3-{3-[1-(7-Chloro-2-cyclopropylmethyl-1-oxo-2,3-dihydro-1H-isoindol-5-yl methyl)-piperidin-4-yl]-propyl}-benzonitrile |
| 19 | 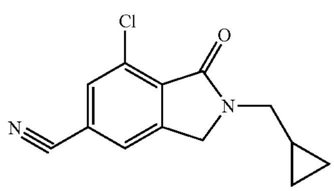 | 7-Chloro-2-cyclopropylmethyl-1-oxo-2,3-dihydro-1H-isoindole-5-carbonitrile |
| 20 | 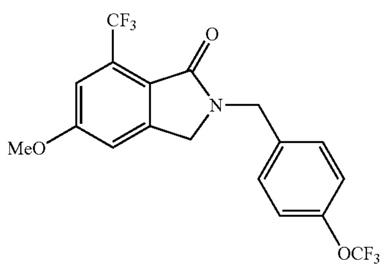 | 5-Fluoro-2-(4-ethyl-benzyl)-7-trifluoro methyl-2,3-dihydro-isoindol-1-one |
| 21 | 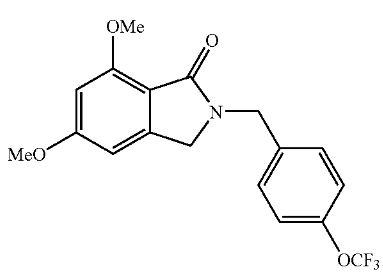 | 5,7-Dimethoxy-2-(4-trifluoromethoxy-benzyl)-2,3-dihydro-isoindol-1-one |

-continued

| Example No. | Structure | Name |
|---|---|---|
| 22 | [Structure with OMe, MeO groups on isoindolinone with N-CH2-phenyl-Cl] | 5,7-Dimethoxy-2-(4-chloro-benzyl)-2,3-dihydro-isoindol-1-one |
| 23 | [Structure with OMe, MeO groups on isoindolinone with N-CH(CH3)-phenyl-Cl] | 5,7-Dimethoxy-2-[1-(4-chloro-phenyl)-ethyl]-2,3-dihydro-isoindol-1-one |

Pharmaceutical Compositions

The compounds of the present invention may be formulated into conventional pharmaceutical composition comprising a compound of formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or table disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

We have discovered that the compounds of the present invention exhibit activity as pharmaceuticals, in particular as modulators of metabotropic glutamate receptors. More particularly, the compounds of the present invention exhibit activity as potentiators of the mGluR2 receptor, and are useful in therapy, in particular for the treatment of neurological and psychiatric disorders associated with glutamate dysfunction in an animal.

More specifically, the neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

The invention thus provides a use of any of the compounds according to formula I, or a pharmaceutically acceptable salt or solvate thereof, for the manufacture of a medicament for the treatment of any of the conditions discussed above.

Additionally, the invention provides a method for the treatment of a subject suffering from any of the conditions discussed above, whereby an effective amount of a compound according to formula I or a pharmaceutically acceptable salt or solvate thereof, is administered to a patient in need of such treatment. The invention also provides a compound of formula I or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses the administration of an effective amount of a compound of the present invention, to mitigate either a pre-existing disease state, acute or chronic, or to mitigate a recurring condition. This definition also encompasses prophylactic therapies for prevention of recurring conditions and continued therapy for chronic disorders.

In use for therapy in a warm-blooded animal such as a human, the compounds of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints. In preferred embodiments of the invention, the route of administration is oral, intravenous, or intramuscular.

The dosage will depend on the route of administration, the severity of the disease, age and weight of the patient and other factors normally considered by the attending physician, who determines the individual regimen and dosage level for a particular patient.

As mentioned above, the compounds described herein may be provided or delivered in a form suitable for oral use, for example, in a tablet, lozenge, hard and soft capsule, aqueous solution, oily solution, emulsion, and suspension. Alternatively, the compounds may be formulated into a topical administration, for example, as a cream, ointment, gel, spray, or aqueous solution, oily solution, emulsion or suspension. The compounds described herein also may be provided in a form that is suitable for nasal administration, for example, as a nasal spray, nasal drops, or dry powder. The compounds can be administered to the vagina or rectum in the form of a suppository. The compounds described herein also may be administered parentally, for example, by intravenous, intravesicular, subcutaneous, or intramuscular injection or infusion. The compounds can be administered by insufflation (for example as a finely divided powder). The compounds may also be administered transdermally or sublingually.

In addition to their use in therapeutic medicine, the compounds of formula I, or salts thereof, are useful as pharmacological tools in the development and standardisation of in vitro and in vivo test systems for the evaluation of the effects of inhibitors of mGluR-related activity in laboratory animals as part of the search for new therapeutics agents. Such animals include, for example, cats, dogs, rabbits, monkeys, rats and mice.

Process for Preparing

Compounds of the present invention can be prepared by various synthetic processes. The selection of a particular process to prepare a given compound is within the purview of the person of skill in the art. The choice of particular structural features and/or substituents may therefore influence the selection of one process over another.

Within these general guidelines, the following processes can be used to prepare exemplary subsets of compounds of this invention. Unless indicated otherwise, the variables described in the following schemes and processes have the same definitions as those given for formula I above.

In one process, for example, a compound of formula Ia:

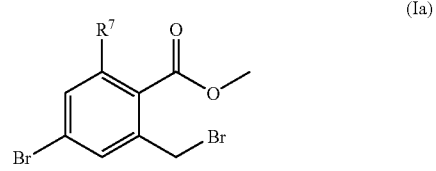

(Ia)

is cyclized in the presence of an amine of the formula $R^1(CR^8CR^9)_nNH_2$ to give a compound of formula Ib:

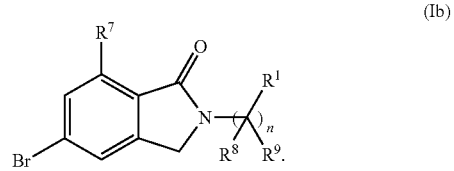

(Ib)

A compound of formula Ib is then cross-coupled with a suitable reagent containing $R^5$ to yield a a compound according to formula Ic:

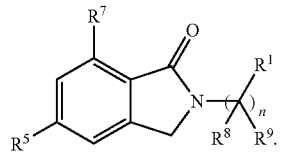

(Ic)

In one embodiment of this process, 5-substituted-7-methyl isoindolones are synthesized as depicted in Scheme 1 below. 4-bromo-2,6-dimethylaniline is converted to the corresponding nitrile under Sandmeyer reaction conditions. The nitrile is then hydrolyzed to the acid in a stepwise fashion. The amide can be obtained by basic hydrolysis. The amide is then diazotized and hydrolyzed with nitrososulphuric acid to provide the benzoic acid, which is subsequently protected as the methyl ester using standard conditions. The benzylic methyl group is monobrominated with N-bromosuccinimide using benzoyl peroxide as the radical initiator. This resultant intermediate is cyclized to the isoindolone with the appropriate amine in the presence of a base such as potassium carbonate. Finally, substituent R⁵ was introduced at C5 of the isoindolone using typical Buchwald, Suzuki or Stille cross-coupling reaction conditions and reagents.

Scheme 1

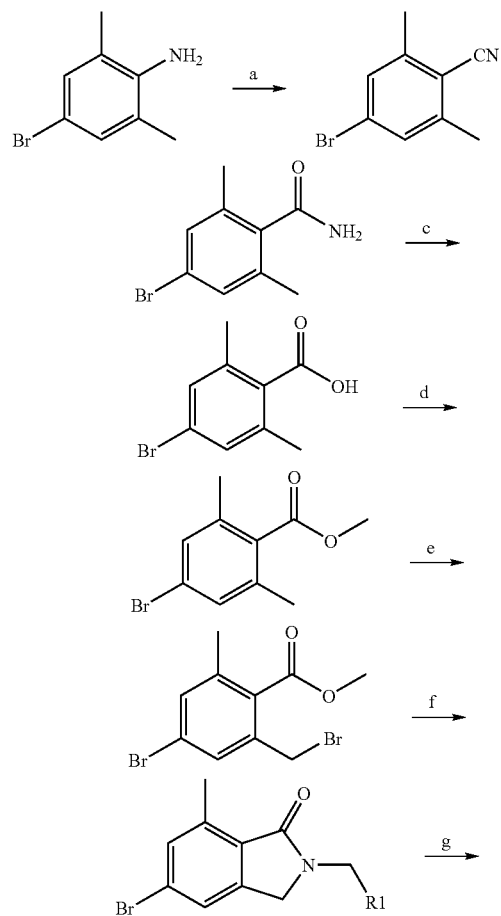

-continued

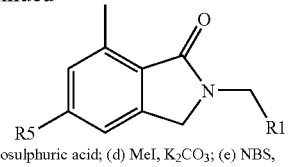

(a) NaCN, CuCN, HCl; (b) NaOH; (c) nitrososulphuric acid; (d) MeI, K₂CO₃; (e) NBS, (PhCO₂)₂; (f) R1CH₂NH₂, K₂CO₃; (g) R5H, BINAP, PdCl₂(dppf), NaOtBu OR R5B(OH)₂, PdCl₂(dppf), K₂CO₃ OR R5SnBu₃, Pd(PPh₃)₄

In another embodiment of this process, 5-substituted-7-chloro isoindolones are synthesized as depicted in Scheme 2 below. 4-bromo-2-methylbenzoic acid is chlorinated ortho to the acid using N-chlorosuccinimide and a palladium catalyst. In the manner analogous to that described above (Scheme 1), this acid was then esterified, brominated, and cyclized to yield the isoindolone intermediate. Substituent R⁵ is introduced similarly.

Scheme 2

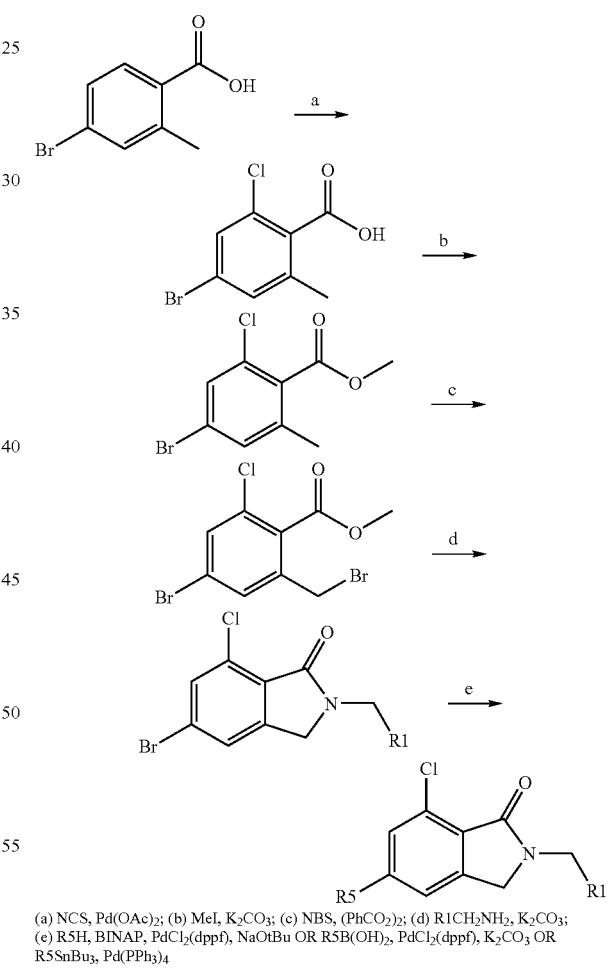

(a) NCS, Pd(OAc)₂; (b) MeI, K₂CO₃; (c) NBS, (PhCO₂)₂; (d) R1CH₂NH₂, K₂CO₃; (e) R5H, BINAP, PdCl₂(dppf), NaOtBu OR R5B(OH)₂, PdCl₂(dppf), K₂CO₃ OR R5SnBu₃, Pd(PPh₃)₄

In yet another embodiment of this process, isoindolones that are substituted with an amide at C5 can be prepared as depicted in Scheme 3 below. Thus, an appropriately substituted 5-bromoisoindolone is converted to the corresponding nitrile using zinc cyanide in the presence of a palladium catalyst. The nitrile is then hydrolyzed under basic conditions to provide the benzoic acid, which was then coupled with various amines using methodologies that are well-known in the art to provide the final compounds.

Scheme 3

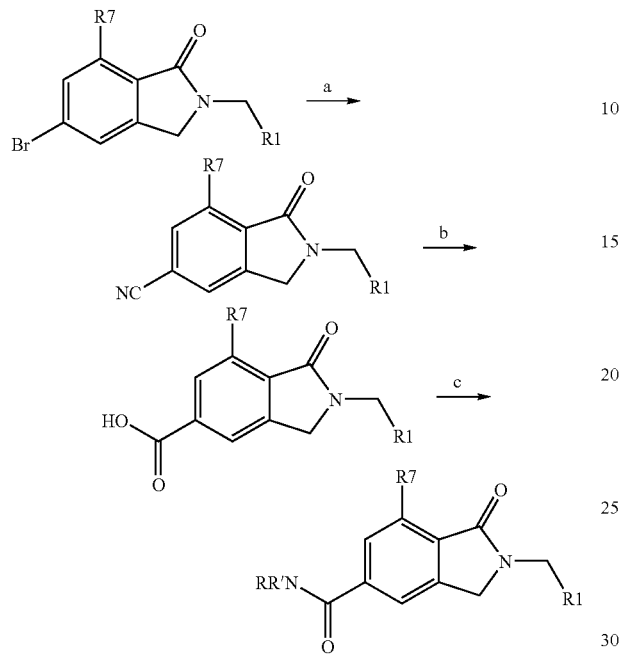

(a) Zn(CN)₂, Pd(PPh₃)₄; (b) NaOH; (c) RR'NH, EDCl

In still another embodiment, the process as described above can be adapted for the preparation of amino-propargyl and amino-alkyl isoindolones. Thus, suitable 5-bromoisoindolones are first subjected to Sonogashira coupling conditions with various propargyl amines as shown in Scheme 4. The resulting alkyne then can be hydrogenated using routine methodologies to provide the amino-alkyl substituted product. In Scheme 4, R and R' correspond to substituents as defined herein for $R^{10}$ and $R^{11}$.

Scheme 4

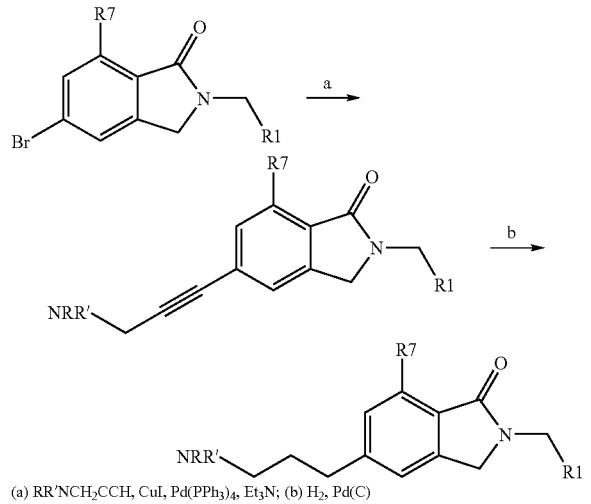

(a) RR'NCH₂CCH, CuI, Pd(PPh₃)₄, Et₃N; (b) H₂, Pd(C)

Another process according to this invention adapts some of the foregoing synthetic methodology for the preparation of compounds bearing N-propargylic substituents. Thus, a compound of the formula Ia:

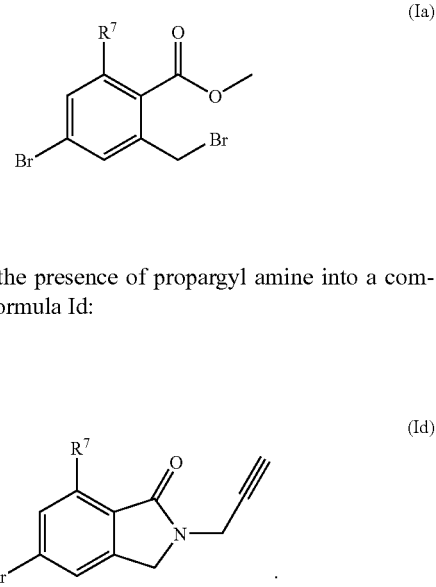

(Ia)

is cyclized in the presence of propargyl amine into a compound of the formula Id:

(Id)

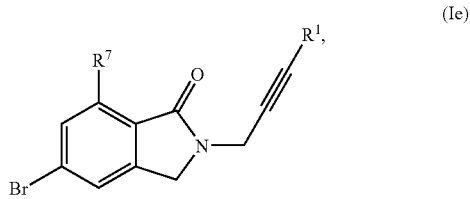

Coupling a compound of formula Id with a reagent comprising $R^1$ gives a compound of formula Ie:

(Ie)

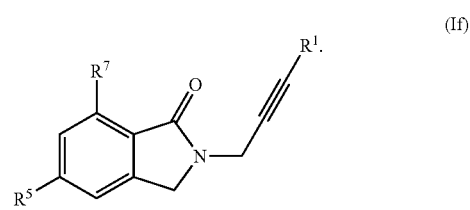

$R^1$ preferably is an aryl group. A compound of formula Ie is then cross-coupled with a reagent comprising $R^5$, thereby yielding a compound according to formula If:

(If)

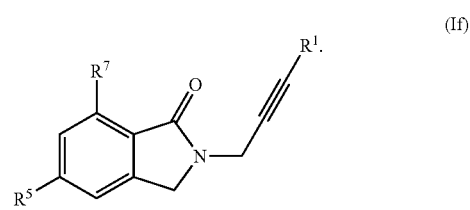

One embodiment of this process is shown in Scheme 5 below. The terminal alkyne is coupled with various aryl groups using standard Sonogashira coupling conditions. Finally, substituent $R^5$ was introduced at C5 using typical Buchwald, Suzuki or Stille cross-coupling reaction conditions as indicated in Scheme 5.

Scheme 5

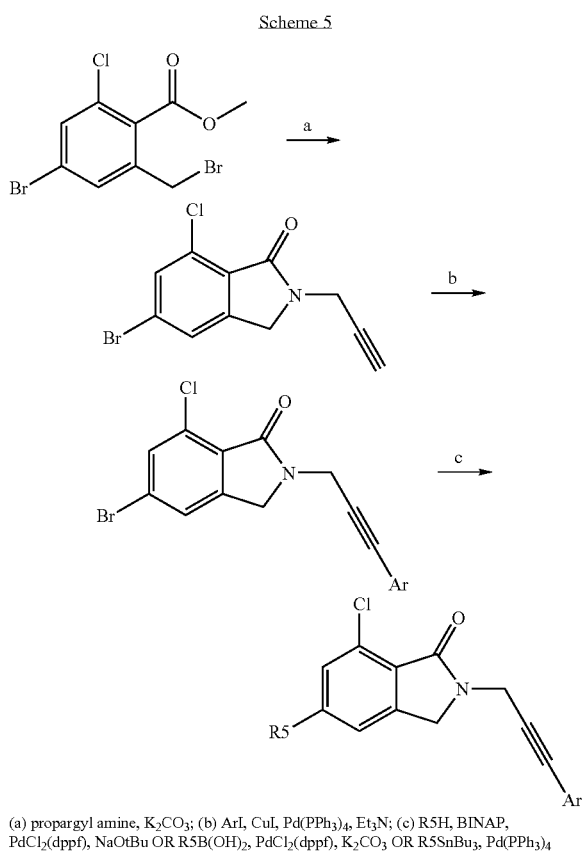

(a) propargyl amine, K₂CO₃; (b) ArI, CuI, Pd(PPh₃)₄, Et₃N; (c) R5H, BINAP, PdCl₂(dppf), NaOtBu OR R5B(OH)₂, PdCl₂(dppf), K₂CO₃ OR R5SnBu₃, Pd(PPh₃)₄

Another process of the invention contemplates the preparation of compounds of formula I that are unsubstituted on the isoindolone aromatic ring. This subset of compounds are be straightforwardly prepared as depicted below in Scheme 6. Thus, phthalimide is reduced, for example with tin under acidic conditions, to provide isoindolinone. This intermediate is alkylated with various electrophiles under basic conditions to provide the desired final products. In Scheme 6, X can be any suitable leaving group such as, for example, halo, such as bromo and iodo; and tosylate.

Scheme 6

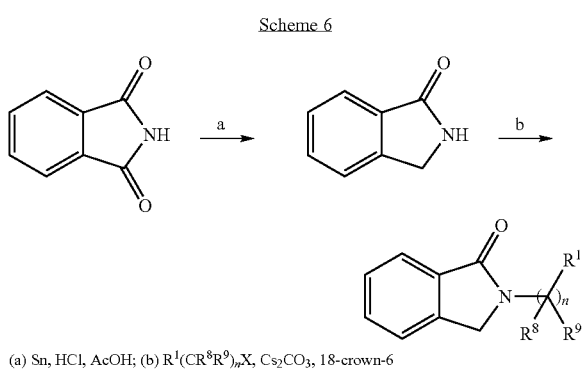

(a) Sn, HCl, AcOH; (b) R¹(CR⁸R⁹)ₙX, Cs₂CO₃, 18-crown-6

Many variations of the foregoing processes and additions thereto appear throughout the examples that follow. The person of ordinary skill in the art thus will appreciate that the compounds of this invention can be prepared by following or adapting one or more of the processes disclosed herein.

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

General Methods

All starting materials are commercially available or earlier described in the literature.

The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet).

Analytical in line liquid chromatography separations followed by mass spectra detections, were recorded on a Waters LCMS consisting of an Alliance 2795 (LC) and a ZQ single quadropole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.), or in 0.1% TFA (aq.).

Preparative reversed phase chromatography was run on a Gilson autopreparative HPLC with a diode array detector using an XTerra MS C8, 19×300 mm, 7 mm as column.

Purification by a chromatotron was performed on rotating silica gel/gypsum (Merck, 60 PF-254 with calcium sulphate) coated glass sheets, with coating layer of 1, 2, or 4 mm using a TC Research 7924T chromatotron.

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns.

Microwave heating was performed in a Smith Synthesizer Single-mode microwave cavity producing continuous irradiation at 2450 MHz (Personal Chemistry AB, Uppsala, Sweden).

The pharmacological properties of the compounds of the invention can be analyzed using standard assays for functional activity. Examples of glutamate receptor assays are well known in the art as described in, for example, Aramori et al., 1992, Neuron, 8:757; Tanabe et al., 1992, Neuron, 8:169; Miller et al., 1995, J. Neuroscience, 15:6103; Balazs, et al., 1997, J. Neurochemistry, 1997, 69:151. The methodology described in these publications is incorporated herein by reference. Conveniently, the compounds of the invention can be studied by means of an assay that measures the mobilization of intracellular calcium, $[Ca^{2+}]_i$ in cells expressing mGluR2.

Fluorometric Imaging Plate Reader (FLIPR) analysis was used to detect allosteric activators of mGluR2 via calcium mobilization. A clonal HEK 293 cell line expressing a chimeric mGluR2/CaR construct comprising the extracellular and transmembrane domains of human mGluR2 and the intracellular domain of the human calcium receptor, fused to the promiscuous chimeric protein $G_{\alpha qi5}$ was used. Activation of this construct by agonists or allosteric activators resulted in stimulation of the PLC pathway and the subsequent mobilization of intracellular $Ca^{2+}$ which was measured via FLIPR analysis. At 24-hours prior to analysis, the cells were trypsinized and plated in DMEM at 100,000 cells/well in black sided, clear-bottom, collagen I coated, 96-well plates. The plates were incubated under 5% $CO_2$ at 37° C. overnight. Cells were loaded with 6 µM fluo-3 acetoxymethylester (Molecular Probes, Eugene Oreg.) for 60 minutes at room temperature. All assays were performed in a buffer containing 126 mM NaCl, 5 mM KCl, 1 mM $MgCl_2$, 1 mM $CaCl_2$, 20 mM Hepes, 0.06M DCG-IV (a Group II mGluR selective agonist), supplemented with 1.0 mg/ml D-glucose and 1.0 mg/ml BSA fraction IV (pH 7.4).

FLIPR experiments were done using a laser setting of 0.8 W and a 0.4 second CCD camera shutter speed. Extracellular fluo-3 was washed off and cells were maintained in 160 µL of buffer and placed in the FLIPR. An addition of test compound (0.01 µM to 30 µM in duplicate) was made after 10 seconds of baseline fluorescent readings were recorded on FLIPR. Fluorescent signals were then recorded for an additional 75 seconds at which point a second addition of DCG-IV (0.2 µM) was made and fluorescent signals were recorded for an additional 65 seconds. Fluorescent signals were measured as the peak height of the response within the sample period. Data was analyzed using Assay Explorer, and $EC_{50}$ and $E_{max}$ values (relative to maximum DCG-IV effect) were calculated using a four parameter logistic equation.

A [$^{35}$S]-GTPγS binding assay was used to functionally assay mGluR2 receptor activation. The allosteric activator activity of compounds at the human mGluR2 receptor were measured using a [$^{35}$S]-GTPγS binding assay with membranes prepared from CHO cells which stably express the human mGluR2. The assay is based upon the principle that agonists bind to G-protein coupled receptors to stimulate GDP-GTP exchange at the G-protein. Since [$^{35}$S]-GTPγS is a non-hydrolyzable GTP analog, it can be used to provide an index of GDP-GTP exchange and, thus, receptor activation. The GTPγS binding assay therefore provides a quantitative measure of receptor activation.

Membranes were prepared from CHO cells stably transfected with human mGluR2. Membranes (30 µg protein) were incubated with test compound (3 nM to 300 µM) for 15 minutes at room temperature prior to the addition of 1 µm glutamate, and incubated for 30 min at 30° C. in 500 µl assay buffer (20 mM HEPES, 100 mM NaCl, 10 mM $MgCl_2$), containing 30 µM GDP and 0.1 nM [$^{35}$S]-GTPγS (1250 Ci/mmol). Reactions were carried out in triplicate in 2 ml polypropylene 96-well plates. Reactions were terminated by vacuum filtration using a Packard 96-well harvester and Unifilter-96, GF/B filter microplates. The filter plates were washed 4×1.5 ml with ice-cold wash buffer (10 mM sodium phosphate buffer, pH 7.4). The filter plates were dried and 35 µl of scintillation fluid (Microscint 20) was added to each well. The amount of radioactivity bound was determined by counting plates on the Packard TopCount. Data was analyzed using GraphPad Prism, and $EC_{50}$ and $E_{max}$ values (relative to the maximum glutamate effect) were calculated using non-linear regression.

Generally, the compounds of the present invention were active in assays described herein at concentrations (or with $EC_{50}$ values) less than 10 µM. For example, compounds of Examples 8.3, 10.4, 11 and 13.7 and have EC50 values 75, 230, 84 and 28 nM, respectively.

Example 1

4,4-Difluorocyclohexanecarboxamide

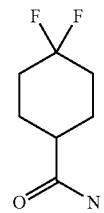

A suspension of ethyl 4,4-difluorocyclohexanecarboxylate (2500 mg, 13 mmol) in ammonium hydroxide (28%, 50 ml) was stirred at 60° C. overnight. After removal of solvent, the residue was washed with water. The precipitate was obtained as product (white solid, 800 mg). $^1$H NMR (300 MHz, $CDCl_3$): δ 5.31-5.45 (br, 2H), 2.02-2.27 (m, 3H), 1.92-2.02 (m, 2H), 1.72-1.87 (m, 4H). The mother liquor was acidified with 1N HCl to pH<1. The compound was extracted with EtOAc. The organic layer was washed with water, brine, dried over anhydrous sodium sulphate, filtered, condensed. 4,4-difluorocyclohexanecarboxylic acid was obtained as a 1200 mg of white solid which was further converted to 4,4-difluorocyclohexanecarboxamide by following procedure.

To a solution of 4,4-difluorocyclohexanecarboxylic acid (1.35 g, 8.22 mmol) in THF (50 ml), 4-methylmorpholine (831 mg, 8.22 mmol)was added at −70° C. followed by isobutyl chloridocarbonate (1140 mg, 8.22 mmol). 10 mins later, ammonium hydroxide (28%, 10 ml) was added. The resulting mixture was allowed to warm up to 0° C. After removal of all solvents, the residue was washed with water, hexanes to provide a 1.06 g of white solid which was 4,4-difluorocyclohexanecarboxamide. Total yield was 82%.

Example 2

[(4,4-Difluorocyclohexyl)methyl]amine

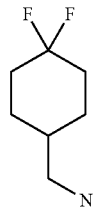

4,4-difluorocyclohexanecarboxamide (1.32 g, 8.10 mmol) was stirred in the solution of lithium borohydrate (1M, 30 ml) under nitrogen overnight. Then, the reaction mixture was refluxed for 4 hours. After cooled to room temperature, it was poured into ice-water slowly. After filtration, the product was extracted with dichloromethane from filtrate. Combined organic layers were water, brine, dried over anhydrous sodium sulphate, filtered and condensed to provide a 934 mg of colorless oil (82%). δ 2.53 (d, 2H), 1.98-2.09 (m, 2H), 1.73-1.82 (m, 6H), 1.17-1.29 (m, 3H).

Example 3

Tert-butyl 4-fluorocyclohexanecarboxylate

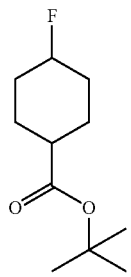

To a solution of tert-butyl 4-hydroxycyclohexanecarboxylate (1500 mg, 7.45 mmol) in dichloromethane (anhydrous, 20 ml), DAST was (1571 mg, 22.4 mmol) added at 0° C. The resulting mixture was stirred at 0° C. for 3 hours. The mixture was diluted with dichloromethane, quenched with sodium bicarbonate. The organic layer was separated, the aqueous phase was extracted with EtOAc. The combined organic layer were washed with water, brine, dried with androus sodium sulphate. The product was purified (flash chromatography, 10 to 20% EtOAc/hexanes) and obtained as a 210 mg of yellow oil (25%). $^1$H NMR (300 MHz, CDCl$_3$): δ 5.60-5.80 (m, 1H), 4.99-5.09 (m, 2H), 4.73 (d, 2H), 3.34 (br, 2H), 2.29-2.32 (m, 2H), 1.44-1.46 (m, 9H).

Example 4

5-Bromo-7-chloro-2-[(4,4-difluorocyclohexyl)methyl]isoindolin-1-one

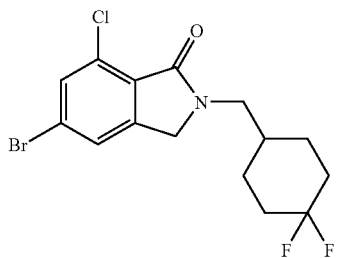

4-Bromo-2-bromomethyl-6-chlorobenzoic acid methyl ester (3.5 g, 9.35 mmol), (4,4-difluorocyclohexyl)methylamine (1.7 g, 11.39 mmol) and K$_2$CO$_3$ (3.15 g, 22.78 mmol) were stirred in toluene (10 mL) at 95° C. for 12 hours. The reaction was partitioned between ethyl acetate and water and the organic layer was washed with brine and dried over anhydrous Na$_2$—SO$_4$. The solvent was removed under reduced pressure and the product was purified by column chromatography (10-25% EtOAc/Hexanes) to afford the title compound as a yellow foam (2.2 g, 45%), $^1$H NMR (300 MHz, CDCl$_3$): 7.58 (s, 1H), 7.50 (s, 1H), 4.36 (s, 2H), 3.48 (d, 2H), 2.10-2.14 (m, 2H), 1.64-1.82 (m, 5H), 1.35-1.447 (m, 2H)

Example 5

7-Chloro-2-[(4,4-difluorocyclohexyl)methyl]-1-oxoisoindoline-5-carbonitrile

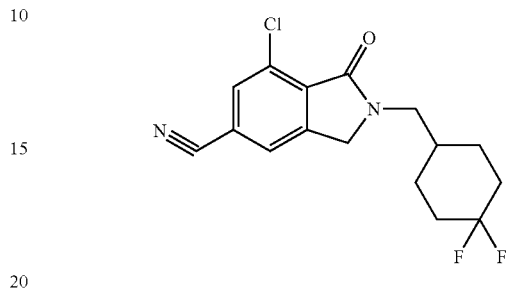

5-bromo-7-chloro-2-[(4,4-difluorocyclohexyl)methyl]isoindolin-1-one (1.14 g, 3.01 mmol) was set stirring in DMF (10 mL) under argon and Zn(CN)$_2$ (389 mg, 3.31 mmol) and Pd(PPh$_3$)$_4$ (347 mg, 0.3 mmol) were added. The reaction was stirred at 80° C. for 1.5 hours. The reaction was partitioned between ethyl acetate and water and the organic layer was washed with brine and dried over anhydrous Na$_2$SO$_4$. The solvent was removed under reduced pressure and the product was purified by column chromatography (40% EtOAc/Hexanes) to afford the title compound as a yellow foam (60 mg, 80%). $^1$H NMR (300 MHz, CDCl$_3$): 7.72 (s, 1H), 7.65 (s, 1H), 4.45 (s, 2H), 3.53 (d, 2H), 2.11-2.15 (m, 2H), 1.66-1.91 (m, 5H), 1.41-1.50 (m, 2H)

Example 6

7-Chloro-5-[5-(chloromethyl)-1,2,4-oxadiazol-3-yl]-2-[(4,4-difluoro-cyclohexyl)methyl] isoindolin-1-one

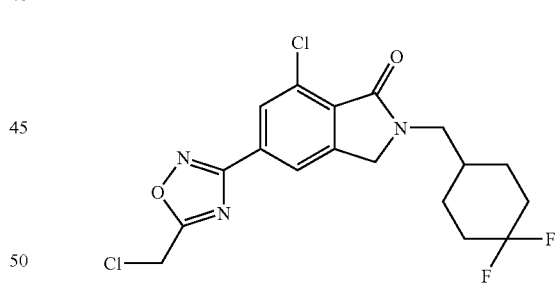

To a solution of 7-Chloro-N-hydroxy-1-oxo-2-[(4,4-difluorocyclohexyl)methyl]-2,3-dihydro-1H-isoindole-5-carboxamidine (450 mg, 1.26 mmol) in acetonitrile (10 ml), chloroacetyl chloride (170 mg, 1.51 mmol) was added, followed by K$_2$CO$_3$ (260 mg, 1.89 mmol). The mixture was stirred overnight. After diluter with EtOAc (20 ml), it was washed with water, brine, dried over anhydrous sodium sulphate, filtered and concentrated to provide a yellow foam. This foam was stirred in DMF (2 ml) at 140° C. for 3 hours. After cooled to room temperature, it was diluted with water (5 ml). The product was extracted with EtOAc. The organic layer was washed with water, brine, dried over anhydrous sodium sulphate, filtered and concentrated. The product was purified by column chromatography (40 to 60% EtOAc in hexanes) to yield the title compound as a white solid

Example 7.1

7-Chloro-N-hydroxy-1-oxo-2-(4-trifluoromethoxy-benzyl)-2,3-dihydro-1H-isoindole-5-carboxamidine

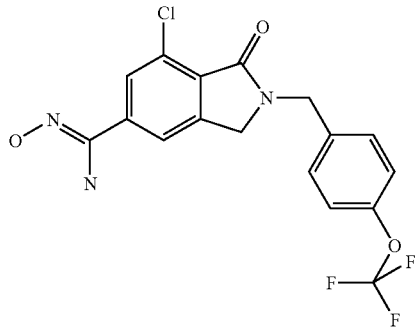

To a suspension of 7-chloro-1-oxo-2-[4-(trifluoromethoxy)benzyl]isoindoline-5-carbonitrile (500 mg, 1.36 mmol) in ethanol (2 ml), 8-hydroxyquinoline (495 mg, 3.41 mmol) was added, followed by a solution of hydroxylamine hydrochloride (199 mg, 2.86 mmol) in water (1 ml) and a solution of sodium carbonate (230 mg, 2.2 mmol) in water (1 ml). The resulting mixture was refluxed for 4 hours. After removal of solvents, the residue was loaded to a flash chromatography. The product was purified (20% EtOAc/hexanes to 2% ammonia in MeOH/EtOAc) and obtained a 500 mg of greenish foam (90%). $^1$H NMR (300 MHz, CDCl$_3$): δ 10.04 (s, 1H) 7.48-7.61 (m, 2H), 7.28-7.36 (m, 2H), 7.17-7.21 (m, 2H), 6.04 (br, 1H), 4.77 (s, 2H), 4.22 (s, 2H).

The following compounds were made in a similar manner:

| Example | Structure | Name | Yield |
|---|---|---|---|
| 7.2 | 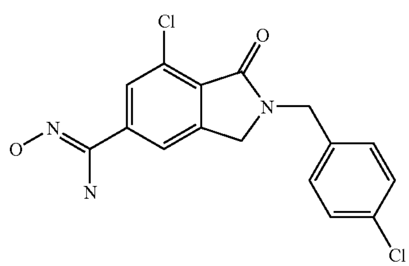 | 7-Chloro-2-(4-chlorobenzyl)-N'-hydroxy-1-oxoisoindoline-5-carboximidamide | 930 mg, (85%), brown solid |
| NMR | 10.04 (s, 1H), 7.76-7.80 (m, 2H), 7.29-7.43 (m, 4H), 6.02 (s, 2H), 4.70 (s, 2H), 4.38 (s, 2H). | | |
| 7.3 | 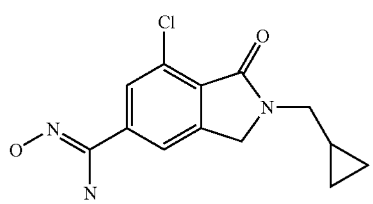 | 7-Chloro-2-(cyclopropylmethyl)-N'-hydroxy-11-oxoisoindoline-5-carboximidamide | 700 mg, (80%), brown solid |
| NMR | 10.01 (s, 1H), 7.77-7.83 (m, 2H), 5.90 (s, 2H), 4.54 (s, 2H), 3.40 (d, 2H), 0.99-1.06 (m, 1H), 0.53-0.58 (m, 2H), 0.33-0.39 (m, 2H). | | |
| 7.4 | 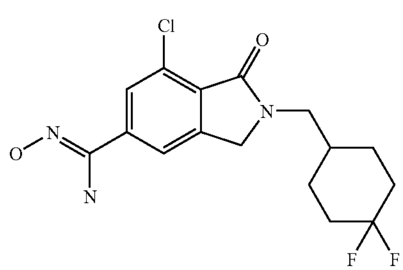 | 7-Chloro-2-[(4,4-difluorocyclohexyl)methyl]-N'-hydroxy-1-oxoisoindoline-5-carboximidamide | 800 mg, (87%), yellow solid |
| NMR | 10.01 (s, 1H), 7.59-4.63 (m, 2H), 4.92 (s, 2H), 4.42 (s, 2H), 3.51 (d, 2H), 2.10-2.15 (m, 1H), 1.61-1.81 (m, 6H), 1.40-1.45 (m, 2H). | | |

Example 8.1

7-Chloro-5-[5-(4-hydroxy-piperidin-1-ylmethyl)-[1,2,4]oxadiazol-3-yl]-2-(4-trifluoromethoxy-benzyl)-2,3-dihydro-isoindol-1-one

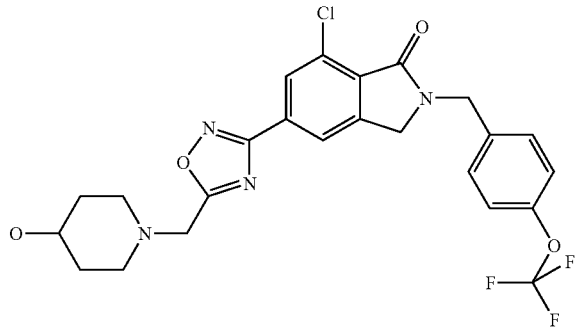

To a mixture of 4-Hydroxy piperidine (9.9 mg, 0.098 mmol), 7-chloro-5-chloromethyl-[1,2,4]oxadiazol-3-yl)-2-(4-trifluoromethoxy-benzyl)-2,3-dihydro-isoindol-1-one (30 mg, 0.065 mmol) and potassium carbonate (27 mg, 0.195 mmol) was added acetonitrile (3.0 mL). The mixture was allowed to stir at room temperature overnight. Water (2.0 mL) was added and the product was extracted with ethyl acetate. The organic layer was washed with water, brine, dried over sodium sulfate, filtered and concentrated. Column chromatography provided the title compound as a yellow oil, 16.7 mg (49%). $^1$H NMR (300 MHz, CDCl$_3$): δ 8.20 (s, 1H), 8.04 (s, 1H), 7.38-7.41 (m, 2H), 7.20-7.23 (m, 2H), 4.82 (s, 2H), 4.34 (s, 2H), 3.95 (s, 2H), 3.75 (br, 1H), 2.90-2.93 (m, 2H), 2.42-2.50 (m, 2H), 1.94-1.99 (m, 2H), 1.64-1.74 (m, 3H)

The following compounds were prepared in a similar manner:

| Example | Structure | Name | Yield |
|---|---|---|---|
| 8.2 | (structure) | 7-Chloro-5-[5-(4-oxo-piperidin-1-ylmethyl)-[1,2,4]oxadiazol-3-yl]-2-(4-trifluoromethoxy-benzyl)-2,3-dihydro-isoindol-1-one | 23.8 mg (70%), yellow oil |
| NMR | 8.19 (s, 1H), 8.04 (s, 1H), 7.37-7.41 (m, 2H), 7.20-7.23 (m, 2H), 4.82 (s, 2H), 4.34 (m, 2H), 4.10 (s, 2H), 3.00 (t, 2H), 2.56 (t, 2H) | | |
| 8.3 | (structure) | 7-Chloro-5-[5-(4-fluoro-piperidin-1-ylmethyl)-[1,2,4]oxadiazol-3-yl]-2-(4-trifluoromethoxy-benzyl)-2,3-dihydro-isoindol-1-one | 22.1 mg (50%), yellow oil |
| NMR | 8.19 (s, 1H), 8.02 (s, 1H), 7.32-7.40 (m, 2H), 7.11-7.19 (m, 2H), 4.79 (s, 2H), 4.30 (s, 2H), 3.94 (s, 2H), 3.75 (br, 1H), 2.85-2.95 (m, 2H), 2.40-2.50 1.85-1.95 (m, 2H), 1.60-1.75 (m, 2H) | | |

-continued

| Example | Structure | Name | Yield |
|---|---|---|---|
| 8.4 | 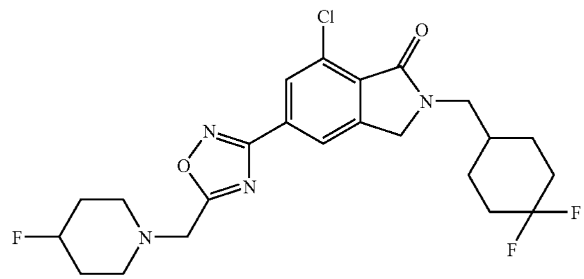 | 7-Chloro-2-(4,4-difluoro-cyclohexylmethyl)-5-[5-(4-fluoro-piperidin-1-ylmethyl)-[1,2,4]oxadiazol-3-yl]-2,3-dihydro-isoindol-1-one | 33.2 mg (95%), white solid |
| NMR | 8.50 (s, 1H), 8.24 (s, 1H), 4.68 (s, 2H), 3.94 (s, 2H), 3.75 (br, 1H), 2.89-3,54 (m, 2H), 2.80-3.00 (m, 2H), 2.45-2.55 (m, 2H), 2.05-2.2 (m, 2H), 1.85-1.95 (m, 3H), 1.35-1.85 (m, 8H) | | |

Example 9.1

4-(2-Cyclopropylmethyl-7-methyl-1-oxo-2,3-dihydro-1H-isoindol-5-ylmethyl)-piperidine-1-carboxylic acid tert-butyl ester

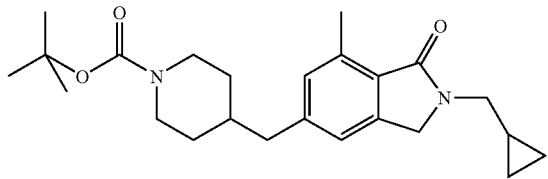

To a purged (Argon) sample of 4-Methylene-piperidine-1-carboxylic acid tert-butyl ester (727 mg, 3.68 mmol) was added 9-BBN (11.32 mL, 5.66 mmol). The mixture was stirred at 60° C. for two hours. After cooling to room temperature this solution was added to 5-Bromo-7-methyl-2-cyclopropylmethyl-2,3-dihydro-isoindol-1-one (794 mg, 2.83 mmol), Pd(dppf)Cl$_2$ (115 mg, 0.142 mmol), DMF (25 mL), potassium carbonate (1.17 g, 8.49 mmol) and water (2.5 mL). The mixture was allowed to stir at 75° C. for 1.5 hours. The mixture was then cooled to room temperature and poured into water (3 mL). The product was extracted with ethyl acetate. The combined organic layers were washed with water three times, brine, dried over sodium sulphate, filtered and concentrated. Column chromatography (30% Ethyl acetate/hexanes) provided the title compound as a light yellow oil (777 mg, 53%). $^1$H NMR (300 MHz, CDCl$_3$): δ 7.01 (s, 1H), 6.94 (s, 1H), 4.39 (s, 2H), 3.42 (d, 2H), 2.68 (s, 3H), 2.57 (s, 2H), 2.54 (d, 2H), 1.70-1.62 (m, 4H), 1.43 (s, 9H), 1.09 (d, 1H), 1.01 (m, 1H), 0.56-0.5 (m, 2H), 0.31-0.29 (m, 2H).

The following compound was prepared in a similar manner:

| Example | Structure | Name | Yield |
|---|---|---|---|
| 9.2 | 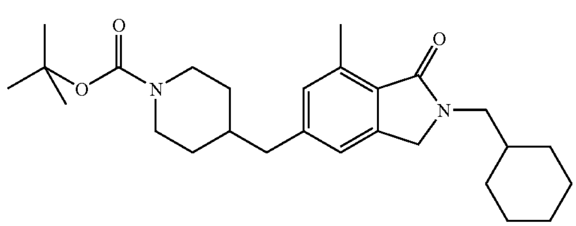 | 4-(2-Cyclohexylmethyl-7-methyl-1-oxo-2,3-dihydro-1H-isoindol-5-ylmethyl)-piperidine-1-carboxylic acid tert-butyl ester | 658 mg 48% colourless solid |
| NMR | 7.00 (s, 2H), 6.97 (s, 1H), 4.31 (s, 2H), 3.42-3.40 (d, 2H), 2.71 (s, 3H), 2.65-2.57 (m, 4H), 1.73-1.61 (m, 9H), 1.47 (s, 9H), 1.25-0.90 (m, 7H) | | |

Example 10.1

2-Cyclopropylrethyl-7-methyl-5-piperidin-4-ylm-ethyl-2,3-dihydro-isoindol-1-one

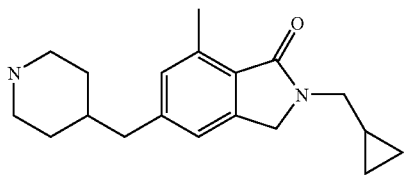

4-[7-Methyl-1-oxo-2-cyclopropylmethyl-2,3-dihydro-1H-isoindol-5-yl]-piperidine-1-carboxylic acid tert-butyl ester (777 mg, 1.95 mmol) was dissolved in formic acid (10 mL) and stirred at room temperature for 0.5 hours. The formic acid was removed under reduced pressure and the product was neutralized with NaHCO$_3$ and extracted with CH$_2$Cl$_2$. The organic layer was washed with brine, dried over anhydrous Na$_2$SO$_4$, filtered and concentrate to afford the title compound (578 mg, 99%) as a brown oil. $^1$H NMR (300 MHz, CDCl$_3$): δ 7.02 (s, 1H), 6.95 (s, 1H), 4.40 (s, 2H), 3.43 (d, 2H), 3.07-3.03 (d, 2H), 2.69 (s, 3H), 2.56-2.38 (m, 4H), 2.38 (br s, 1H), 1.64-1.61 (m, 4H), 1.19-1.15 (m, 2H), 1.02 (m, 1H), 0.57-0.53 (m, 2H), 0.34-0.30 (m, 2H).

The following compounds were prepared in a similar manner:

| Example | Structure | Name | Yield |
|---|---|---|---|
| 10.2 | 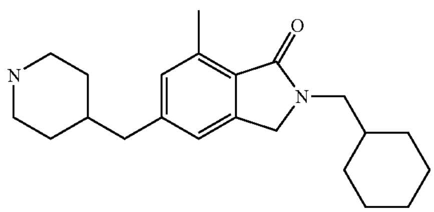 | 2-Cyclohexylmethyl-7-methyl-5-piperidin-4-ylmethyl-2,3-dihydro-isoindol-1-one | 501 mg<br>99%<br>bron oil |
| NMR | 7.01 (s, 1H), 6.97 (s, 1H), 4.30 (s, 2H), 3.42-3.40 (d, 2H), 3.14-3.10 (d, 2H), 2.71 (s, 3H), 2.63-2.57 (m, 4H), 1.73-1.67 (m, 9H), 1.30-1.19 (m, 4H), 1.05-1.02 (m, 3H). | | |
| 10.3 | 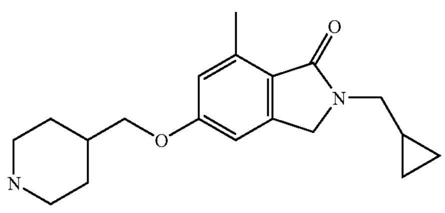 | 2-Cyclopropylmethyl-7-methyl-5-(piperidin-4-ylmethoxy)-2,3-dihydro-isoindol-1-one | 294 mg<br>94%<br>yellow solid |
| NMR | 6.74 (s, 1H), 6.70 (s, 1H), 4.38 (s, 2H), 3.83-3.81 (d, 2H), 3.43-3.41 (d, 2H), 3.17-3.13 (d, 2H), 2.71-2.64 (m, 5H), 2.37 (br s, 1H), 1.95-1.82 (m, 3H), 1.36-1.28 (m, 2H), 1.02 (m, 1H), 0.57-0.53 (m, 2H), 0.33-0.29 (m, 2H). | | |
| 10.4 | 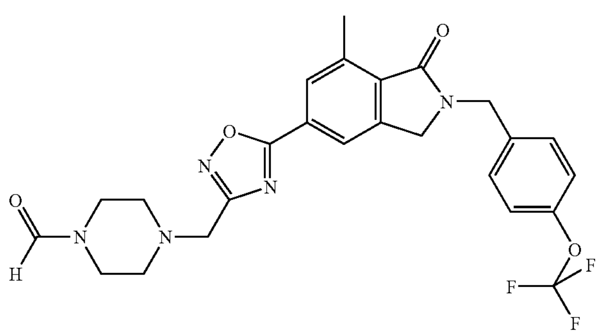 | 4-{5-[7-Methyl-1-oxo-2-(4-trifluoromethoxy-benzyl)-2,3-dihydro-1H-isoindol-5-yl]-[1,2,4]oxadiazol-3-ylmethyl}-piperazine-1-carbaldehyde | 30 mg<br>52%<br>yellow solid |
| NMR | 8.05 (s, 2H), 8.00 (s, 1H), 7.39-7.38 (d, 2H), 7.23-7.20 (d, 2H), 4.82 (s, 2H), 4.34 (s, 2H), 3.84 (s, 2H), 3.66-3.63 (m, 2H), 3.48-3.45 (m, 2H), 2.86 (s, 3H), 2.68-2.62 (m, 4H). | | |

Example 11

2-Cyclopropylmethyl-5-[1-(2-fluorobenzyl)-piperidin-4-ylmethyl]-7-methyl-2,3-dihydro-isoindol-1-one

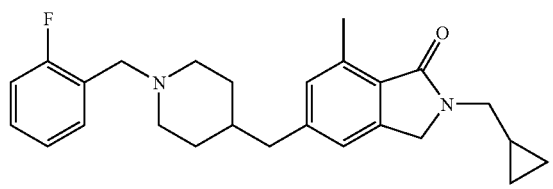

To a mixture of 2-Fluorobenzyl bromide (47 µL, 0.377 mmol), 7-methyl-5-piperidin-4-ylmethyl-2-cyclohexylpropyl-2,3-dihydro-isoindol-1-one (75 mg, 0.251 mmol) and potassium carbonate (104 mg, 0.753 mmol) was added acetonitrile (3.0 mL). The mixture was stirred at 80° C. for 4 hours. 1 scoop of Sodium tert-butoxide (~200 mg) was added and stirring continued overnight at 80° C. The mixture was cooled to room temperature, water (2.0 mL) was added and the product was extracted with ethyl acetate. The organic layer was washed with water, brine, dried over sodium sulfate, filtered and concentrated. Column chromatography provided the title compound as a yellow oil (6.6 mg, 6%). $^1$H NMR (300 MHz, CDCl$_3$): δ 7.38 (m, 1H), 7.23-7.13 (m, 1H), 7.11-7.00 (m, 3H), 6.96 (s, 1H), 4.41 (s, 2H), 3.61 (s, 2H), 3.46-3.44 (d, 2H), 2.95-2.92 (d, 2H), 2.70 (s, 3H), 2.59-2.57 (d, 2H), 2.01-1.98 (t, 2H), 1.65-1.61 (m, 3H), 1.38-1.27 (m, 2H), 1.04 (m, 1H), 0.60-0.55 (m, 2H), 0.36-0.32 (m, 2H).

Example 12.1

2-Cyclohexylmethyl-7-methyl-5-(1-pyrimidin-2-ylmethyl-piperidin-4-ylmethyl)-2,3-dihydro-isoindol-1-one

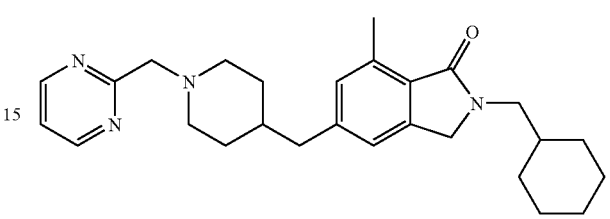

To a mixture of 2-Chloromethylpyrimidine (32 mg, 0.247 mmol), 2-Cyclohexylmethyl-7-methyl-5-piperidin-4-ylmethyl-2,3-dihydro-isoindol-1-one (56 mg, 0.164 mmol) and cesium carbonate (160 mg, 0.492 mmol) was added acetonitrile (3.0 mL). The mixture was allowed to stir at room temperature overnight. Water (2.0 mL) was added and the product was extracted with ethyl acetate. The organic layer was washed with water, brine, dried over sodium sulfate, filtered and concentrated. Column chromatography provided the title compound as a yellow oil (48 mg, 69%). $^1$H NMR (300 Adz, CDCl$_3$): δ 8.76-8.72 (d, 2H), 7.18 (t, 1H), 6.99 (s, 1H), 6.95 (s, 1H), 4.30 (s, 2H), 3.78 (s, 2H), 3.40-3.37 (d, 2H), 2.97-2.93 (d, 2H), 2.70 (s, 3H), 2.58-2.56 (d, 2H), 2.10-2.05 (t, 2H), 1.71-1.42 (m, 10H), 1.26-1.13 (m, 4H), 1.09-0.98 (m, 2H).

The following compounds were prepared in a similar manner:

| Example | Structure | Name | Yield |
| --- | --- | --- | --- |
| 12.2 | 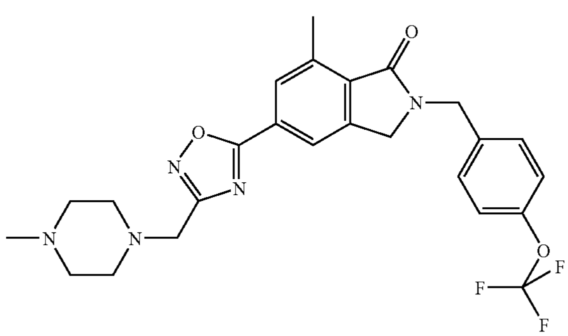 | 7-Methyl-5-[3-(4-methyl-piperazin-1-ylmethyl)-[1,2,4]oxadiazol-5-yl]-2--(4-trifluoromethoxy-benzyl)-2,3-dihydro-isoindol-1-one | 50 mg<br>88%<br>colourless solid |
| NMR | 8.04 (s, 1H), 7.99 (s, 1H), 7.39-7.34 (c, 2H), 7.22-7.19 (d, 1H), 4.80 (s, 2H), 4.33 (s, 2H), 3.79 (s, 3H), 2.78-2.68 (br s, 4H), 2.62-2.51 (br s, 4H), 2.30 (s, 3H). | | |

-continued

| Example | Structure | Name | Yield |
|---|---|---|---|
| 12.3 | 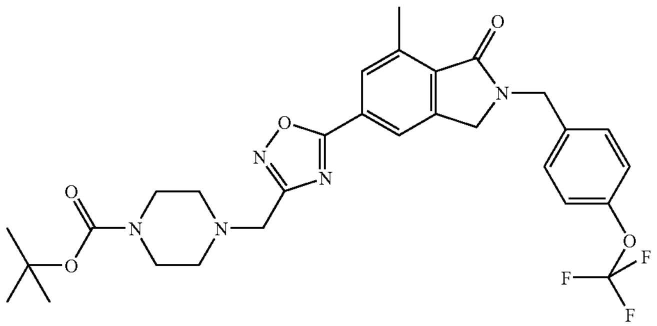 | 4-{5-[7-Methyl-1-oxo-2-(4-trifluoromthoxy-benzyl)-2,3-dihydro-1H-isoindol-5-yl]-[1,2,4]oxadiazol-3-ylmethyl}-piperazine-1-carboxylic acid tert-butyl ester | 60 mg colourless solid |
| NMR | 8.05 (s, 1H), 8.00 (s, 1H), 7.36-7.36 (s, 2H), 7.23-7.20 (d, 2H), 4.81 (s, 2H), 4.34 (s, 2H), 3.80 (s, 2H)3.52-3.47 (m, 4H), 2.85 (s, 3H), 2.60-2.57 (m, 4H), 1.46 (s, 9H). | | |

Example 13.1

2-Cyclopropylmethyl-5-[1-(3-fluoro-benzyl)-piperidin-4-ylmethyl]-7-methyl-2,3-dihydro-isoindol-1-one

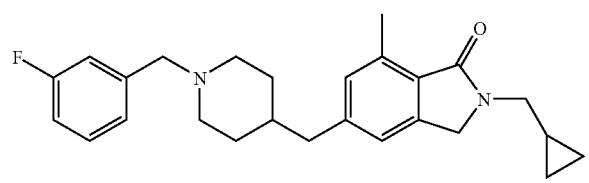

To a solution of 2-Cyclopropylmethyl-7-methyl-5-piperidin-4-ylmethyl-2,3-dihydro-isoindol-1-one (30 mg, 0.110 mmol) in methanol (2 mL) was slowly added acetic acid (1 mL). After stirring at room temperature for 5 minutes, 3-Fluoro-benzaldehyde (12.8 µL, 0.121 mmol) and sodium cyanoborohydride (8 µL, 0.111 mmol) were added dropwisely. The mixture stirred at room temperature for 2 hours and was neutralized with saturated sodium bicarbonate (10 mL). The aqueous mixture was extracted with dichloromethane and the organics were dried over anhydrous sodium sulfate, filtered and concentrated. Column chromatography (10-40% ethyl acetate in hexanes) provided the title compound as a yellow oil. $^1$H NMR (300 MHz, CDCl$_3$): δ 7.70-7.23 (m, 1H), 7.09-7.03 (m, 3H), 6.97-6.92 (m, 2H), 4.41 (s, 2H), 3.48-3.44 (m, 4H), 2.88-2.85 (d, 2H), 2.71 (s, 3M), 2.60-2.57 (d, 2H), 1.93 (t, 2H), 1.64-1.50 (m, 3H), 1.36-1.28 (m, 2H), 1.04 (m, 1H), 0.60-0.55 (m, 2H), 0.34-0.32 (m, 2H)

The following compounds were prepared in a similar manner:

| Example | Structure | Name | Yield |
|---|---|---|---|
| 13.2 | 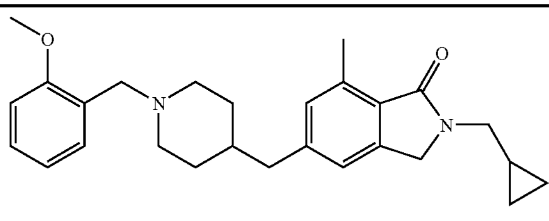 | 2-Cyclopropylmethyl-5-[1-(2-methoxybenzyl)-piperidin-4-ylmethyl]-7-methyl-2,3-dihydro-isoindol-1-one | 7.3 mg 11% colourless oil |
| NMR | 7.36-7.34 (d, 1H), 7.23-7.20 (m, 1H), 7.02 (s, 1H), 6.96-6.85 (m, 3H), 4.41 (s, 2H), 3.81 (s, 3H), 3.55 (s, 2H), 3.46-3.43 (d, 2H), 2.95-2.91 (d, 2H), 2.70 (s, 3H), 2.60-2.57 (d, 2H), 1.98 (t, 2H), 1.70 (br s, 2H), 1.63-1.59 (m, 3H), 1.39-1.37 (m, 2H), 1.04 (m, 1H), 0.60-0.55 (m, 2H), 0.36-0.32 (m, 2H) | | |
| 13.3 | 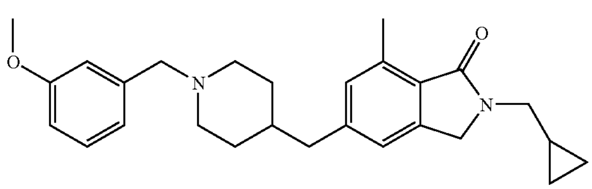 | 2-Cyclopropylmethyl-5-[1-(3-mthoxybenzyl)-piperidin-4-ylmethyl]-7-methyl-2,3-dihydro-isoindol-1-one | 40 mg 60% yellow oil |
| NMR | 7.26-7.20 (m, 1H), 7.03 (s, 1H), 6.97 (s, 1H), 6.91-6.89 (m, 3H), 4.41 (s, 2H), 3.82 (s, 3H), 3.47-3.44 (m, 4H), 2.90-2.86 (d, 2H), 2.71 (s, 3H), 2.59-2.57 (d, 2H), 1.92 (t, 2H), 1.64-1.59 (m, 3H), 1.36-1.35 (m, 2H), 1.04 (m, 1H), 0.59-0.55 (m, 2H), 0.36-0.32 (m, 2H) | | |

-continued

| Example | Structure | Name | Yield |
|---|---|---|---|
| 13.4 | 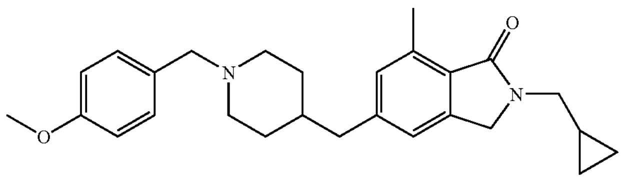 | 2-Cyclopropylmethyl-5-[1-(4-methoxybenzyl)-piperidin-4-ylmethyl]-7-methyl-2,3-dihydro-isoindol-1-one | 23 mg 34% yellow oil |
| NMR | 7.23-7.21 (d, 2H), 7.02 (s, 1H), 6.96 (s, 1H), 6.87-6.84 (, 2H), 4.41 (s, 2H), 3.82 (s, 3H), 3.46-3.44 (m, 4H), 2.89-2.85 (d, 2H), 2.70 (s, 3H), 2.58-2.56 (d, 2H), 1.91 (t, 2H), 1.63-1.59 (m, 3H), 1.34-1.32 (m, 2H), 1.04 (m, 1H), 0.59-0.55 (m, 2H), 0.36-0.32 (m, 2H) | | |
| 13.5 | 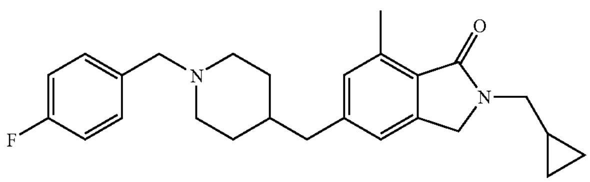 | 2-Cyclopropylmethyl-5-[1-(4-fluorobenzyl)-piperidin-4-ylmethyl]-7-methyl-2,3-dihydro-isoindol-1-one | 36 mg 35% light yellow oil |
| NMR | 7.29-7.24 (m, 2H), 7.02-6.97 (m, 4H), 4.41 (s, 2H), 3.61 (s, 2H), 3.46-3.44 (m, 4H), 2.87-2.83 (d, 2H), 2.70 (s, 3H), 2.59-2.57 (d, 2H), 1.90-1.86 (t, 2H), 1.63-1.59 (m, 3H), 1.34-1.30 (m, 2H), 1.04 (m, 1H), 0.60-0.55 (m, 2H), 0.35-0.32 (m, 2H) | | |
| 13.6 | 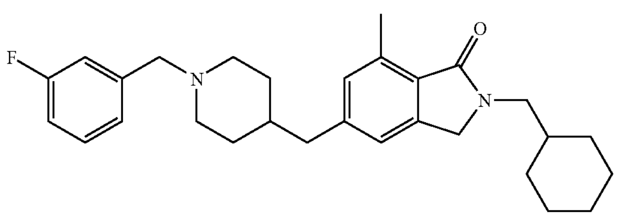 | 2-Cyclohexylmethyl-5-[1-(3-fluoro-benzyl)-piperidin-4-ylmethyl]-7-methyl-2,3-ddihydro-isoindol-1-one | 34 mg 43% colourless oil |
| NMR | 7.30-7.23 (m, 1H), 7.09-7.04 (m, 2H), 7.00-6.92 (m, 3H), 4.29 (s, 2H), 3.48 (s, 2H), 3.41-3.39 (d, 2H), 2.88-2.84 (d, 2H), 2.70 (s, 3H), 2.59-2.57 (d, 2H), 1.86-1.89 (t, 2H), 1.73-1.60 (m, 8H), 1.35-1.19 (m, 6H), 1.05 (m, 2H) | | |
| 13.7 | 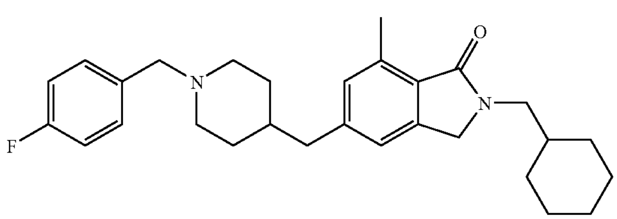 | 2-Cyclohexylmethyl-5-[1-(4-fluoro-benzyl)-piperidin-4-ylmethyl]-7-methyl-2,3-dihydro-isoindol-1-one | 26 mg 33% light yellow oil |
| NMR | 7.29-7.24 (m, 2H), 7.03-6.96 (m, 4H), 4.29 (s, 2H), 3.45 (s, 2H), 3.41-3.39 (d, 2H), 2.87-2.83 (d, 2H), 2.70 (s, 3H), 2.58-2.56 (d, 2H), 1.90-1.86 (t, 2H), 1.76-1.59 (m, 9H), 1.34-1.19 (m, 5H), 1.06 (m, 2H) | | |

| Example | Structure | Name | Yield |
|---|---|---|---|
| 13.8 | 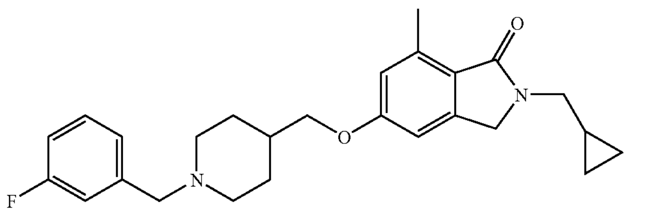 | 2-Cyclopropyomethyl-5-[1-(3-fluorobenzyl)-piperidin-4-ylmethoxy]-7-methyl-2,3-dihydro-isoindol-1-one | 27 mg 26% yellow oil |
| NMR | 7.32-7.25 (m, 1H), 7.11-7.08 (m, 2H), 6.98-6.95 (m, 1H), 6.75-6.72 (d, 2H), 4.38 (s, 2H), 3.86-3.84 (d, 2H), 3.52 (s, 2H), 3.44-3.42 (d, 2H), 2.96-2.92 (d, 2H), 2.70 (s, 3H), 2.07-2.04 (t, 2H), 1.85-1.82 (m, 3H), 1.45 (m, 2H), 1.04 (m, 1H), 0.59-0.55 (m, 2H), 0.35-0.31 (m, 2H) | | |
| 13.9 | 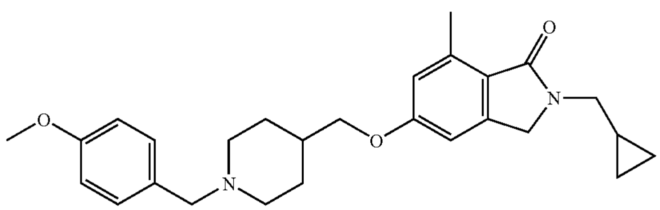 | 2-Cyclopropylmethyl-5-[1-(4-methoxy-benzyl)-piperidin-4-ylmethoxy]-7-methyl-2,3-dihydro-isoindol-1-one | 24 mg 39% yellow oil |
| NMR | 7.28-7.22 (m, 1H), 7.11-7.08 (m, 2H), 6.94-6.91 (m, 2H), 6.83-6.81 (d, 1H), 6.79-6.71 (d, 2H), 4.38 (s, 2H), 3.86-3.83 (m, 5H), 3.52 (s, 2H), 3.44-3.42 (d, 2H), 2.98-2.94 (d, 2H), 2.70 (s, 3H), 2.06-1.99 (t, 2H), 1.85-1.82 (m, 3H), 1.46-1.42 (m, 2H), 1.03 (m, 1H), 0.59-0.56 (m, 2H), 0.35-0.31 (m, 2H) | | |

Example 14

2-Cyclopropylmethyl-5-iodo-7-methyl-2,3-dihydro-isoindol-1-one

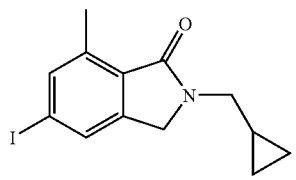

To a solution of 5-Bromo-7-methyl-2-cyclopropylmethyl-2,3-dihydro-isoindol-1-one (1.0 g, 3.56 mmol) in butanol (10 ml), (1R,2R)-N,N'-dimethylcyclohexane-1,2-diamine (204 mg, 1.42 mmol), copper(I) iodide (140 mg, 0.714 mmol) and sodium iodide (1.08 g, 14.3 mmol) were added. The resulting mixture was stirred at 120° C. overnight. After cooling, the mixture was diluted with ethyl acetate, washed with water, brine, dried over anhydrous sodium sulphate, filtered, concentrated. Column chromatography (30% EtOAc/Hexanes) provided the title compound (1.07 g, 92%) as a colourless solid. $^1$H NMR (300 MHz, CDCl$_3$): δ 7.65 (s, 1H), 7.59 (s, 1H), 4.42 (s, 2H), 3.46-3.44 (d, 2H), 2.70 (s, 3H), 1.04-1.02 (m, 1H), 0.61-0.57 (m, 2H), 0.34-0.31 (m, 2H)

Example 15

5-(1-Benzyl-pyrrolidin-3-ylamino)-7-methyl-2-(4-trifluoromethoxy-benzyl)-2,3-dihydro-isoindol-1-one

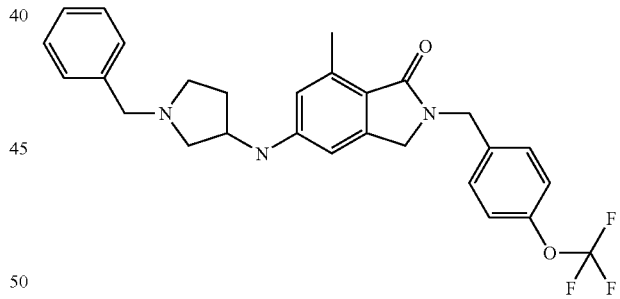

3-Amino-1-benzyl-pyrrolidine (57 mg, 0.325 mmol), 5-Bromo-7-methyl-2-(4-trifluoromethoxybenzyl)-2,3-dihydro-isoindol-1-one (100 mg, 0.25 mmol), NaO$^t$Bu (168 mg, 1.75 mmol), BINAP (16 mg, 0.025 mmol) and Pd$_2$(dba)$_3$ (23 mg, 0.025 mmol) were dissolved in anhydrous toluene (5 mL). The mixture was immersed in a 110° C. oil bath. After eighteen hours, the reaction was cooled and poured into water and extracted with ethyl acetate. The organic phase was washed with brine, dried over MgSO$_4$, filtered and concentrated. The compound was purified by column chromatography (50% EtOAc/Hexanes) to provide the title compound as a yellow gum (87 mg, 70%). $^1$H NMR (300 MHz, CDCl$_3$): δ 7.24-7.34 (m, 7H), 7.18 (d, 2H), 6.34 (d, 2H), 4.72 (s, 2H), 4.33 (d, 1H), 4.12 (s, 2H), 4.04 (m, 1H), 3.64 (collapsed dd, 2H), 2.75-2.83 (m, 2H), 2.66 (s, 3H), 2.58 (dd, 1H), 2.45 (ddd, 1H), 2.32-2.42 (m, 1H), 1.67-1.70 (m, 1H).

Example 16.1

7-Methyl-5-[5-(4-methyl-piperazin-1-ylmethyl)-pyridin-3-yl]-2-(4-trifluoromethoxybenzyl)-2,3-dihydro-isoindol-1-one

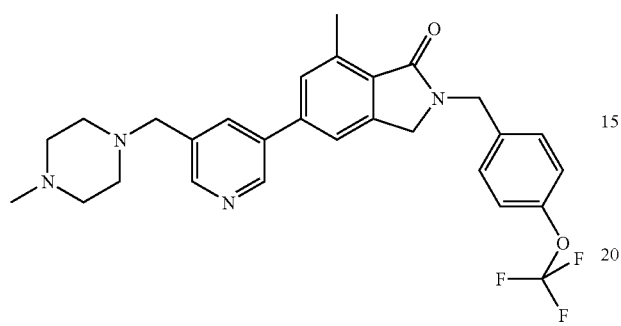

Methanesulfonic acid 5-[7-methyl-1-oxo-2-(4-trifluoromethoxy-benzyl)-2,3-dihydro-1H-isoindol-5-yl]-pyridin-3-ylmethyl ester (36 mg, 0.071 mmol) was dissolved in THF (5 mL). N-Methyl piperazine (24 uL, 0.213 mmol) was added and the mixture stirred at 50° C. for 18 hrs. The mixture was cooled, diluted with water, and extracted with ethyl acetate. The organics were washed with brine, dried over anhydrous sodium sulfate, filtered and concentrated. Column chromatography (5% 2M $NH_3$ in $MeOH/CH_2Cl_2$) provided the title compound (24 mg, 67%) as a yellow oil. $^1H$ NMR (300 MHz, $CDCl_3$): δ 8.73 (s, 1H), 8.56 (s, 1H), 7.86 (s, 1H), 7.42 (d, 2H), 7.37 (d, 2H), 7.19 (d, 2H), 4.82 (s, 2H), 4.32 (s, 2H), 3.60 (s, 2H), 2.85 (s, 3H), 2.52-2.42 (br s, 8H), 2.30 (s, 3H).

The following compound was prepared in a similar manner:

Example 17.1

4-{4-[7-Chloro-1-oxo-2-(4-trifluoromethoxy-benzyl)-2,3-dihydro-1H-isoindol-5-ylmethyl]-piperidin-1-ylethyl}-benzonitrile

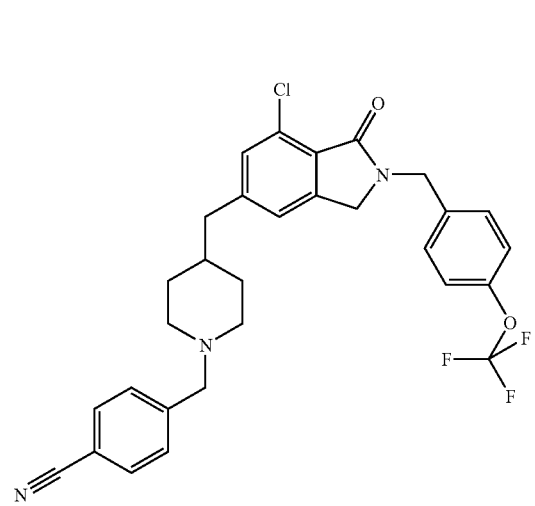

To a mixture of 4-Cyano-benzyl bromide (12 mg, 0.06 mmol), 7-chloro-5-piperidin-4-ylmethyl-2-(4-trifluoromethoxy-benzyl)-2,3-dihydro-isoindol-1-one (30.0 mg, 0.06 mmol) and potassium carbonate (42 mg, 0.3 mmol) was added acetonitrile (3.0 mL). The mixture was allowed to stir at room temperature overnight. Water (2.0 mL) was added and the product was extracted with ethyl acetate. The organic layer was washed with water, brine, dried over sodium sul-

| Example | Structure | Name | Yield |
|---|---|---|---|
| 16.2 | 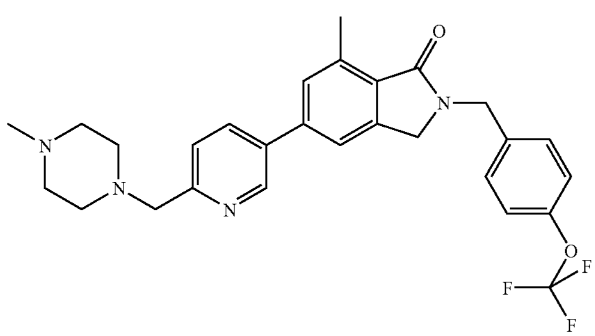 | 7-Methyl-5-[6-(4-methyl-piperazin-1-ylmethyl)-pyridin-3-yl]-2-(4-trifluoromethoxy-benzyl)-2,3-dihydro-isoindol-1-one | 48 mg, 80% brown oil |
| NMR | 8.78 (s, 1H), 7.85 (s, 1H), 7.50 (d, 1H), 7.40-7.34 (m, 4H), 7.20 (d, 2H), 4.81 (s, 2H), 4.32 (s, 2H), 3.73 (s, 2H), 2.84 (s, 3H), 2.60-2.52 (br d, 8H), 2.31 (s, 3H) | | | fate, filtered and concentrated. Column chromatography provided the title compound as a brown oil (39.0 mg, 99%). $^1$H NMR (300 MHz, CDCl$_3$): δ 7.60 (d, 2H), 7.27-7.59 (m, 4H), 7.17-7.20 (m, 3H), 7.05 (s, 1H), 4.77 (s, 2H), 4.22 (s, 2H), 3.53 (s, 2H), 2.80-2.84 (m, 2H), 2.58-2.60 (m, 2H), 1.91 (t, 21, 1.56-1.62 (m, 3H), 1.27-1.34 (m, 2H).

The following compounds were prepared in a similar manner:

| Example | Structure | Name | Yield |
|---|---|---|---|
| 17.2 | 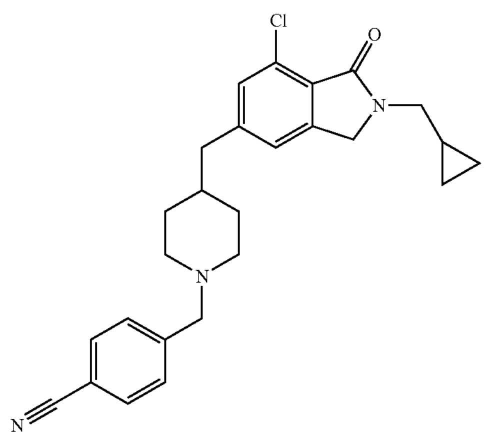 | 4-[4-(7-Chloro-2-cyclopropylmethyl-1-oxo-2,3-dihydro-1H-isoindol-5-ylmethyl)-piperidine-1-ylmethyl]-benzonitrile | 21.1 mg, 82.4%, brown oil |
| NMR | 7.59-7.62 (m, 2H), 7.45 (d, 2H), 7.18 (s, 1H), 7.11 (s, 1H), 4.43 (s, 2H), 3.53 (s, 2H), 3.46 (d, 2H), 2.81-2.85 (m, 2H), 2.60-2.62 (m, 2H), 1.92-1.99 (m, 2H), 1.50-1.64 (m, 3H), 1.27-31.35 (m, 2H), 0.98-1.05 (m, 1H), 0.55-0.60 (m, 2H), 0.33-0.35 (m, 2H) | | |
| 17.3 | 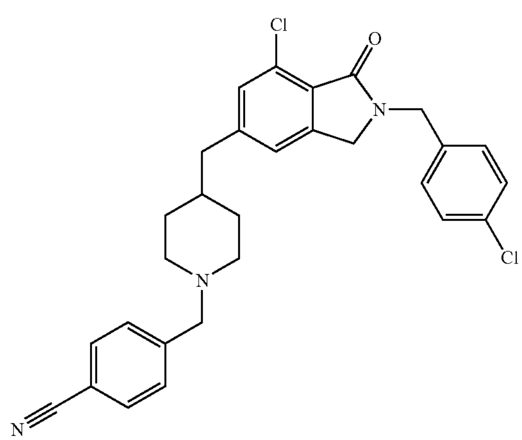 | 4-{4-[7-Chloro-2-(4-chloro-benzyl)-1-oxo-2,3-dihydro-1H-isoindol-5-ylmethyl]-piperidin-1-ylmethyl}-benzonitrile | 81.8 mg, 97.1%, yellow oil |
| NMR | 7.58-7.62 (m, 2H), 7.42-7.50 (m, 2H), 7.24-7.32 (m, 4H), 7.18 (s, 1H), 7.04 (s, 1H), 4.73 (s, 2H), 4.19 (s, 2H), 3.51 (s, 2H), 2.79-2.83 (m, 2H), 2.57-59 (m, 2H), 1.90-1.97 (m, 2H), 1.49-1.61 (m, 2H), 1.24-1.37 (m, 3H) | | |

-continued

| Example | Structure | Name | Yield |
|---|---|---|---|
| 17.4 | 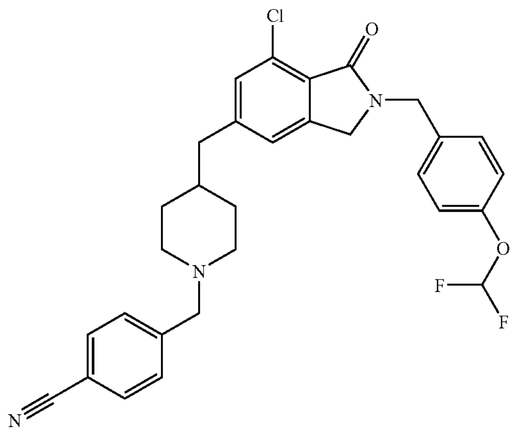 | 4-{4-[7-Chloro-2-(4-difluoromethoxy-benzyl)-1-oxo-2,3-dihydro-1H-isoindol-5-ylmethyl]-piperidin-1-ylmethyl}-benzonitrile | 35.2 mg, 72.9%, yellow oil |
| NMR | 7.59-7.61 (m, 2H), 7.42-7.45 (m, 2H), 7.30-7.35 (m, 2H), 7.19 (s, 1H), 7.05-7.11 (m, 3H), 6.26-6.75 (t, 1H), 4.75 (s, 2H), 4.21 (s, 2H), 3.52 (s, 2H), 2.79-2.83 (m, 2H), 2.58-2.60 (m, 2H), 1.88-1.98 (m, 2H), 1.51-1.62 (m, 3H), 1.25-1.37 (m, 2H) | | |
| 17.5 | 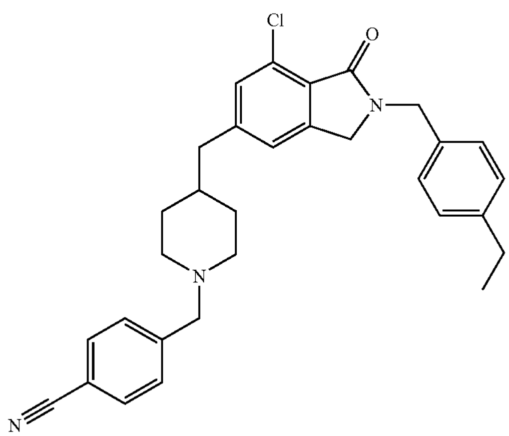 | 4-{4-[7-Chloro-2-(4-ethyl-benzyl)-1-oxo-2,3-dihydro-1H-isoindol-5-yl-methyl]-piperidin-1-ylmethyl}-benzonitrile | 16.2 mg, 43.3%, yellow oil |
| NMR | 7.59-7.62 (m, 2H), 7.42-7.48 (m, 2H), 7.24-7.28 (m, 2H), 7.16-7.18 (m, 3H), 7.02 (s, 1H), 4.74 (s, 2H), 4.19 (s, 2H), 3.52 (s, 2H), 2.79-2.83 (m, 2H), 2.57-2.68 (m, 4H), 1.90-1.98 (m, 2H), 1.51-1.61 (m, 3H), 1.21-1.36 (m, 5H) | | |

Example 18.1

4-{4-[7-Chloro-1-oxo-2-(4-trifluoromethoxy-benzyl)-2,3-dihydro-1H-isoindol-5-ylmethyl]-piperazin-1-methyl}-nicotinonitrile

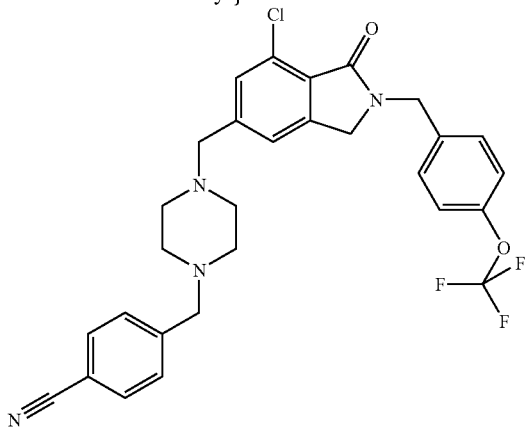

4-(piperazin-1-ylmethyl)benzonitrile (30 mg, 0.094 mmol) was dissolved in dichloromethane (2.0 mL) and 7-Chloro-1-oxo-2-(4-trifluoromethoxy-benzyl)-2,3-dihydro-1H-isoindole-5-carbaldehyde (20.0 mg, 0.054 mmol) was added. The mixture was stirred for ten minutes and sodium triacetoxy borohydride (16.1 mg, 0.076 mmol) was added and the reaction was allowed to stir overnight. The reaction was then diluted with dichloromethane, washed with saturated sodium bicarbonate and brine, dried over sodium sulfate, filtered and concentrated. Column chromatography (20% MeOH/EtOAc) provided the title compound as a yellow oil (17.9 mg, 32%). $^1$H NMR (300 MHz, CDCl$_3$): δ 7.60-7.63 (m, 2H), 7.34-7.47 (m, 5H), 7.27-7.28 (m, 1H), 7.18-7.21 (m, 2H), 4.78 (m, 2H), 4.24 (s, 2H), 3.55-3.57 (m, 4H), 2.48-2.53 (m, 8H).

The following compound was prepared in a similar manner:

| Example | Structure | Name | Yield |
|---|---|---|---|
| 18.2 | 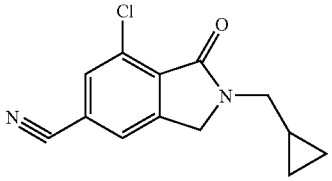 | 3-{3-[1-(7-Chloro-2-cyclopropylmethyl-1-oxo-2,3-dihydro-1H-isoindol-5-ylmethyl)-piperidin-4-yl]-propyl}-benzonitrile | 13 mg, 70.3%, yellow oil |
| NMR | 7.41-7.50 (3H), 7.34-7.38 (m, 2H), 4.44 (s, 2H), 3.52 (s, 2H), 3.46 (d, 2H), 2.84-2.87 (m, 2H), 2.64 (t, 2H), 1.85-1.98 (m, 3H), 1.65-1.68 (m, 4H), 1.26-1.30 (m, 4H), 1.02-1.08 (m, 1H), 0.55-0.61 (m, 2H), 0.33-0.37 (m, 2H) | | |

Example 19

7-Chloro-2-cyclopropylmethyl-1-oxo-2,3-dihydro-1H-isoindole-5-carbonitril

5-Bromo-7-chloro-2-cyclopropylmethyl-2,3-dihydro-isoindol-1-one (360 mg, 1.20 mmol) was set stirring in DM (15 mL) under argon and Zn(CN)$_2$ (154 mg, 1.32 mmol) and Pd(PPh$_3$)$_4$ (139 mg, 0.12 mmol) were added. The reaction was stirred at 80° C. for 1.5 hours. The reaction was partitioned between ethyl acetate and water and the organic layer was washed with brine and dried over anhydrous Na$_2$SO$_4$. The solvent was removed under reduced pressure and the product was purified by column chromatography (40% EtOAc/Hexanes) to afford a yellow solid (142.6 mg, 82%). $^1$H NMR (300 MHz, CDCl$_3$): δ 7.53 (s, 2H), 7.36 (d, 2H), 7.22 (s, 2H), 4.80 (s, 2H), 4.30 (s, 2H), 2.81 (s, 3H).

Example 20

7-Trifluoromethyl-5-methoxy-2-(4-trifluoromethoxy-benzyl)-2,3-dihydro-isoindol-1-one

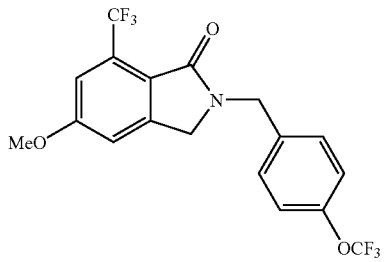

A mixture of 7-trifluoromethyl-5-bromo-2-(4-trifluoromethoxy-benzyl)-2,3-dihydro-isoindol-1-one (0.060 g, 0.15 mmol), and 30% sodium methoxide-methanol (0.21 mL) in methanol (4 mL) was stirred at 100° C. for 1 h. Workup and silica gel column chromatography using 30% ethyl acetate in hexane afforded 7-trifluoromethyl-5-methoxy-2-(4-trifluoromethoxy-benzyl)-2,3-dihydro-isoindol-1-one (0.043 g, 70%). $^1$H NMR (300 MHz, CDCl$_3$): δ (ppm) 3.88 (s, 3H), 4.25 (s, 2H), 4.76 (s, 2H), 7.02 (s, 1H), 7.17 (d, 2H), 7.28 (s, 1H), 7.37 (d, 2H).

Example 21

5,7-Dimethoxy-2-(4-trifluoromethoxy-benzyl)-2,3-dihydro-isoindol-1one

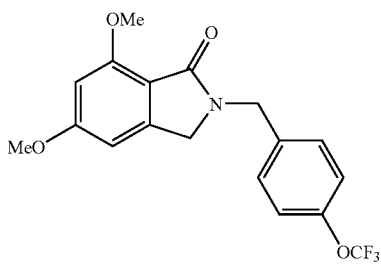

To a solution of 4-bromo-5,7-Dimethoxy-2-(4-trifluoromethoxy-benzyl)-2,3-dihydro-isoindol-1 one (0.200 g, 0.45 mmol) in benzene under N2 atmosphere was added 2,2'-azobis(2-methyl proponitrile) AIBN (5.0 mg), followed by tributyl tin hydride (0.238 mL, 0.9 mmol). The resulting mixture was refluxed in an oil bath for 2 h. The reaction was monitored by GC-MS for the disappearance of starting mate rial. The reaction mixture was cooled to room temperature and stirred with potassium fluoride (200 mg) for 45 min. The solids were filtered and the filtrate was concentrated. The resulting material was purified using column chromatography (typically 40% ethyl acetate in hexanes) to give 5,7-Dimethoxy-2-(4-trifluoromethoxy-benzyl)-2,3-dihydro-isoindol-1one (0.106 g, 64%). ¹H NMR (300 MHz, CDCl₃): δ (ppm) 3.82 (s, 3H), 3.95 (s, 3H), 4.17 (s, 2H), 4.72 (s, 2H), 6.43 (d, 2H), 7.16 (d, 2H), 7.32 (d, 2H). GC-MS: m/z 367 (M)⁺, 349 (M-18)⁺.

Example 22

5,7-Dimethoxy-2-(4-chloro-benzyl)-2,3-dihydro-isoindol-1one

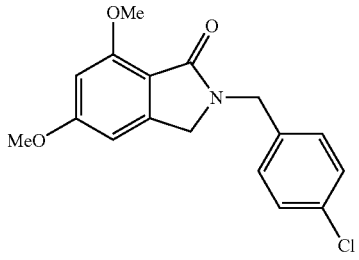

To a solution of 4-bromo-5,7-Dimethoxy-2-(4-chloro-benzyl)-2,3-dihydro-isoindol-1one (0.100 g, 0.25 mmol) in benzene under N2 atmosphere was added 2,2'-azobis(2-methyl proponitrile) AIBN (5.0 mg), followed by tributyl tin hydride (0.132 mL, 0.5 mmol). The resulting mixture was refluxed in an oil bath for 2 h. The reaction was monitored by GC-MS for the disappearance of starting material. The reaction mixture was cooled to room temperature and stirred with potassium fluoride (200 mg) for 45 min. The solids were filtered and the filtrate was concentrated. The resulting material was purified using column chromatography (typically 40% ethyl acetate in hexanes) to give 5,7-Dimethoxy-2-(4-chloro-benzyl)-2,3-dihydro-isoindol-1one (0.035 g, 44%). ¹H NMR (300 MHz, CDCl₃): δ (ppm) 3.82 (s, 3H), 3.95 (s, 3H), 4.15 (s, 2H), 4.69 (s, 2H), 6.43 (d, 2H), 7.25 (m, 4H). GC-MS: m/z 317 (M)⁺, 299 (M-18)⁺.

Example 23

5,7-Dimethoxy-2-[1-(4-chloro-phenyl)-ethyl]-2,3-dihydro-isoindol-1one

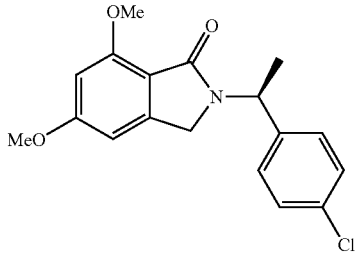

To a solution of 4-bromo-5,7-Dimethoxy-2-[1-(4-chloro-phenyl)-ethyl]-2,3-dihydro-isoindol-1one (0.112 g, 0.27 mmol) in benzene under N2 atmosphere was added 2,2'-azobis(2-methyl proponitrile) AIBN (5.0 mg), followed by tributyl tin hydride (0.145 mL, 0.55 mmol). The resulting mixture was refluxed in an oil bath for 2 h. The reaction was monitored by GC-MS for the disappearance of starting material. The reaction mixture was cooled to room temperature and stirred with potassium fluoride (200 mg) for 45 min. The solids were filtered and the filtrate was concentrated. The resulting material was purified using column chromatography (typically 40% ethyl acetate in hexanes) to give 5,7-Dimethoxy-2-[1-(4-chloro-phenyl)-ethyl]-2,3-dihydro-isoindol-1one (0.056 g, 63%). ¹H NMR (300 MHz, CDCl₃): δ (ppm) 1.43 (d, 3H), 3.63 (s, 3H), 3.68 (d, 1H), 3.74 (s, 3H), 3.99 (d, 1H), 5.53 (q, 1H), 6.23 (dd, 2H), 7.15 (m, 4H). GC-MS: m/z 331 (M)⁺, 316 (M-15)⁺.

What is claimed is:
1. A compound selected from the group consisting of:
  7-Chloro-2-[(4,4-difluorocyclohexyl)methyl]-1-oxoisoindoline-5-carbonitrile,
  7-Chloro-5-[5-(4-hydroxy-piperidin-1-ylmethyl)[1,2,4]oxadiazol-3-yl]-2-(4-trifluoromethoxy-benzyl)-2,3-dihydro-isoindol-1-one,
  7-Chloro-5-[5-(4-oxo-piperidin-1-ylmethyl)-[1,2,4]oxadiazol-3-yl]-2-(4-trifluoromethoxy-benzyl)-2,3-dihydro-isoindol-1-one,
  7-Chloro-5-[5-(4-fluoro-piperidin-1-ylmethyl)[1,2,4]oxadiazol-3-yl]-2-(4-trifluoromethoxy-benzyl)-2,3-dihydro-isoindol-1-one,
  7-Chloro-2-(4,4-difluoro-cyclohexyl-methyl)-5-[5-(4-fluoro-piperidin-1-ylmethyl)-[1,2,4]oxadiazol-3-yl]-2,3-dihydro-isoindol-1-one,
  2-Cyclopropylmethyl-5-[1-(2-fluorobenzyl)-piperidin-4-ylmethyl]-7-methyl-2,3-dihydro-isoindol-1-one,
  2-Cyclopropylmethyl-5-[1-(3-fluoro-benzyl)-piperidin-4-yl methyl]-7-methyl-2,3-dihydro-isoindol-1-one,
  2-Cyclopropylmethyl-5-[1-(2-methoxy-benzyl)-piperidin-4-ylmethyl]-7-methyl-2,3-dihydro-isoindol-1-one,
  2-Cyclopropylmethyl-5-[1-(3-methoxy-benzyl)-piperidin-4-ylmethyl]-7-methyl-2,3-dihydro-isoindol-1-one,
  2-Cyclopropylmethyl-5-[1-(4-methoxy-benzyl)-piperidin-4-ylmethyl]-7-methyl-2,3-dihydro-isoindol-1-one,
  2-Cyclopropylmethyl-5-[1-(4-fluoro-benzyl)-piperidin-4-ylmethyl]-7-methyl-2,3-dihydro-isoindol-1-one,
  2-Cyclohexylmethyl-5-[1-(3-fluoro-benzyl)-piperidin-4-ylmethyl]-7-methyl-2,3-dihydro-isoindol-1-one,
  2-Cyclohexylmethyl-5-[1-(4-fluoro-benzyl)-piperidin-4-ylmethyl]-7-methyl-2,3-dihydro-isoindol-1-one,
  2-Cyclopropylmethyl-5-[1-(3-fluoro-benzyl)-piperidin-4-ylmethoxy]-7-methyl-2,3-dihydro-isoindol-1-one,
  2-Cyclopropylmethyl-5-[1-(4-methoxybenzyl)-piperidin-4-ylmethoxy]-7-methyl-2,3-dihydro-isoindol-1-one,
  5-(1-Benzyl-pyrrolidin-3-ylamino)-7-methyl-2-(4-trifluoromethoxy-benzyl)-2,3-dihydro-isoindol-1-one,
  4-{4-[7-Chloro-1-oxo-2-(4-trifluoromethoxy-benzyl)-2,3-dihydro-1H-isoindol-5-ylmethyl]-piperidin-1-ylmethyl}-benzonitrile,
  4-[4-(7-Chloro-2-cyclopropylmethyl-1-oxo-2,3-dihydro-1H-isoindol-5-ylmethyl)-piperidine-1-ylmethyl]-benzonitrile,
  4-{4-[7-Chloro-2-(4-chloro-benzyl)-1-oxo-2,3-dihydro-1H-isoindol-5-ylmethyl]-piperidin-1-ylmethyl}-benzonitrile,
  4-{4-[7-Chloro-2-(4-difluoromethoxy-benzyl)-1-oxo-2,3-dihydro-1H-isoindol-5-ylmethyl]-piperidin-1-ylmethyl}-benzonitrile,
  4-{4-[7-Chloro-2-(4-ethyl-benzyl)-1-oxo-2,3-dihydro-1H-isoindol-5-ylmethyl]-piperidin-1-ylmethyl}-benzonitrile,

4-{4-[7-Chloro-1-oxo-2-(4-trifluoromethoxy-benzyl)-2,3-dihydro-1H-isoindol-5-ylmethyl]-piperazin-1-methyl}-nicotinonitrile, 3-{3-[1-(7-Chloro-2-cyclopropylmethyl-1-oxo-2,3-dihydro-1H-isoindol-5-ylmethyl)-piperidin-4-yl]-propyl}-benzonitrile, 7-Chloro-2-cyclopropylmethyl-1-oxo-2,3-dihydro-1H-isoindole-5-carbonitrile, 5-Fluoro-2-(4-ethyl-benzyl)-7-trifluoromethyl-2,3-dihydro-isoindol-1-one, 5,7-Dimethoxy-2-(4-trifluoromethoxy-benzyl)-2,3-dihydro-isoindol-1-one, 5,7-Dimethoxy-2-(4-chloro-benzyl)-2,3-dihydro-isoindol-1-one, and 5,7-Dimethoxy-2-[1-(4-chloro-phenyl)-ethyl]-2,3-dihydro-isoindol-1-one;

or a pharmaceutically acceptable salt, optical isomer, or combination thereof.

2. A pharmaceutical composition comprising a compound, a pharmaceutically acceptable salt, an optical isomer, or combination thereof according to claim 1 and a pharmaceutically acceptable carrier or excipient.

3. A method for the treatment of schizophrenia comprising administering to a subject in need thereof a therapeutically effective amount of a compound, a pharmaceutically acceptable salt, an optical isomer, or combination thereof according to claim 1.

4. A method for the treatment of schizophrenia comprising administering to a subject in need thereof a therapeutically effective amount of, a pharmaceutical composition according to claim 2.

* * * * *